(12) United States Patent
Miller

(10) Patent No.: US 7,579,515 B2
(45) Date of Patent: Aug. 25, 2009

(54) INCREASING GAMETE PRODUCTION WITH A GENE SWITCH

(75) Inventor: William L. Miller, Cary, NC (US)

(73) Assignee: North Carolina State University, Raleigh, NC (US)

(*) Notice: Subject to any disclaimer, the term of this patent is extended or adjusted under 35 U.S.C. 154(b) by 360 days.

(21) Appl. No.: 10/534,953

(22) PCT Filed: Dec. 10, 2003

(86) PCT No.: PCT/US03/39236

§ 371 (c)(1), (2), (4) Date: Oct. 4, 2005

(87) PCT Pub. No.: WO2004/061077

PCT Pub. Date: Jul. 22, 2004

(65) Prior Publication Data

US 2006/0064764 A1     Mar. 23, 2006

(51) Int. Cl.
*A01K 67/027*   (2006.01)
*A01K 67/033*   (2006.01)
*A61K 49/00*    (2006.01)
*C12N 15/00*    (2006.01)

(52) U.S. Cl. .................. 800/18; 800/8; 800/21
(58) Field of Classification Search .......... 800/8, 800/18, 21
See application file for complete search history.

(56) References Cited

U.S. PATENT DOCUMENTS

| 5,589,362 | A  | 12/1996 | Bujard et al. |
|---|---|---|---|
| 5,650,298 | A  | 7/1997  | Bujard et al. |
| 5,654,138 | A  | 8/1997  | Lerman et al. |
| 5,866,755 | A  | 2/1999  | Bujard et al. |
| 5,922,927 | A  | 7/1999  | Bujard et al. |
| 6,136,954 | A  | 10/2000 | Bujard et al. |
| 6,200,778 | B1 | 3/2001  | Treco et al. |
| 6,242,667 | B1 | 6/2001  | Bujard et al. |
| 6,252,136 | B1 | 6/2001  | Bujard et al. |
| 6,271,348 | B1 | 8/2001  | Bujard et al. |
| 6,569,681 | B1 | 5/2003  | Ivanov |

OTHER PUBLICATIONS

Niemann, 1998, Transg. Res. 7, pp. 73-75.*
Cameron, E, 1997, Recent Advances in trasngenic technology, Molec. Biol. 7, p. 253-265.*
Matthaei, 2007, J Physiol, 582.2:481-488.*
McTavish et al Endocrinology, 2007, 148:4432-4439.*
International Preliminary Examination Report (IPER). International Application No. PCT/US03/39236. Mailed on Sep. 28, 2005.
Kato et al.; Multiple binding sites for nuclear proteins of the anterior pituitary are located in the 5'- flanking region of the porcine follicle-stimulating hormone (FSH) β-subunit gene, 1999, 158:69-78.
Kumar et al.; "Gonadotrope-specific expression of the human follicle-stimulating hormone beta-subunit gene in pituitaries of transgenic mice" *Mol. Endocrinol.* 6:1 81-90 (1992). (Abstract Only).
Database GenEmbl, Accession No. PIGFSHBS, Harai, T. et al., (2000).
International Search Report for PCT/US03/39236; Date of Mailing Sep. 10, 2004).

* cited by examiner

*Primary Examiner*—Valarie Bertoglio
(74) *Attorney, Agent, or Firm*—Myers Bigel Sibley & Sajovec, P.A.

(57) ABSTRACT

A method of enhancing the production of gametes in a transgenic non-human animal is carried out by: (a) providing a transgenic non-human animal comprising cells that contain: (i) a response element; (ii) a nucleic acid encoding FSHβ operatively associated with the response element; (iii) an FSHβ promoter; (iv) an FSHβ locus control region operatively associated with the FSHβ promoter; and (v) a nucleic acid encoding a ligand-controllable receptor operatively associated with the FSHβ promoter, wherein the receptor binds to the response element in the presence of the ligand when expressed in a host cell; and (b) administering the ligand to the animal in an amount effective to (i) stimulate the production of FSHβ in the animal above that found in a corresponding untransformed type animal; and (ii) stimulate the production of gametes in the animal to a level greater than that found in the corresponding untransformed animal.

8 Claims, 3 Drawing Sheets

INCREASING GAMETE PRODUCTION WITH A GENE SWITCH

GOVERNMENT SUPPORT

This invention was made with Government support under Grant No. 99-35203-7661 from the Department of Agriculture. The United States Government has certain rights to this invention.

FIELD OF THE INVENTION

The present invention concerns methods of increasing gamete production, e.g., ovulation, in animals such as pigs, sheep, rats and mice, along with compounds and compositions useful for carrying out such methods.

BACKGROUND OF THE INVENTION

Follicle stimulating hormone (FSH) is an α/β heterodimer produced only in pituitary gonadotropes, which comprise 3-8% of all pituitary cells. It is named for its ability to stimulate follicle growth and maturation in females. Follicle stimulating hormone stimulates the granulosa cells that surround and nurture the developing oocyte (egg) in the follicle. Spermatogenesis also relies heavily on FSH which induces sertoli cell division in early life. In later life, FSH works in conjunction with testosterone to stimulate sertoli cells to nurture spermatogonia as they develop into sperm. A number of hormones from the hypothalamus, gonads and the pituitary itself, help regulate FSH.

Current technology for increasing ovulation and birthing rates in mammals involves the timed injections of relatively expensive hormones that act like FSH, followed by an injection of human chorionic gonadotropin for ovulation. Increasing ovulation is useful when oocytes are collected from animals for the purpose of being injected with specific genes to produce valuable transgenic offspring or from elite breeding animals for subsequent in vitro fertilization and implantation into a foster parent. Increasing ovulation is also useful for animals such as pigs, where it is desirable to increase the litter size of breeding animals so that the corresponding numbers of breeding animals that must be maintained can be reduced. Increasing litter size is also useful for endangered species where the number of breeding animals in captivity is small. Accordingly, it would be extremely useful to provide a simple and effective approach for increasing the production of gametes in animals.

SUMMARY OF THE INVENTION

FSHβ Locus control regions. Certain aspects of the present invention relate to the locus control regions discovered by applicants. Thus, a first aspect of the present invention is an isolated nucleic acid active as an FSHβ locus control region. A further aspect of the present invention is an isolated nucleic acid construct comprising at least one locus control region as described above operatively associated with a promoter. The promoter may be a heterologous promoter or homologous promoter, and where a homologous promoter the isolated nucleic acid may or may not include intervening segments. A nucleic acid of interest may be coupled to and operatively associated with the promoter in the construct.

A further aspect of the present invention is a method of transforming a host cell, comprising: (a) providing a nucleic acid construct as described above, and then (b) introducing the construct into the host cell (e.g., by lipofection or microinjection). In preferred embodiments a nucleic acid of interest is operatively associated with the promoter, and the nucleic acid of interest is transcribed, and preferably translated and expressed, in the host cell.

A further aspect of the present invention is a recombinant host cell containing a nucleic acid construct as described above. In one embodiment, the host cell is a gonadotrope cell, and the nucleic acid of interest encodes a detectable marker protein or peptide such as luciferase. Such cells are useful in bioassays for determining the activity of compounds that stimulate gonadotrope cells.

A further aspect of the present invention method of making a non-human transgenic animal, comprising the steps of: (a) providing a nucleic acid construct as described above, the construct preferably comprising a nucleic acid of interest operatively associated with the promoter; (b) introducing (e.g., by microinjection or lipofection) the nucleic acid construct into a mammalian oocyte or other suitable embryonic cell; (c) implanting the oocyte or other suitable embryonic cell into suitable host, such as a pseudopregnant female host; and then (d) raising the transgenic animal to viability from the oocyte or other suitable embryonic cell in the host; the transgenic animal preferably comprising anterior pituitary cells (particularly gonadotrope cells) that contain and transcribe the nucleic acid of interest.

A further aspect of the present invention is a transgenic non-human animal, the animal comprising anterior pituitary cells that contain a nucleic acid construct as described above, the construct further comprising a nucleic acid of interest operatively associated with the promoter, with the anterior pituitary cells transcribing the nucleic acid of interest (e.g., a mutated tet receptor; luciferase).

Switches incorporating FSHβ LCRs. Additional aspects of the present invention relate to the implementations of genetic switches as discovered by applicant. Thus, one aspect of the present invention is a recombinant nucleic acid, comprising: (a) a response element (e.g., a tet operator); and (b) a nucleic acid encoding FSHβ operatively associated with the response element. Preferably the recombinant nucleic acid further comprises (c) an FSHβ promoter; (d) an FSHβ locus control region operatively associated with the FSHβ promoter; and (e) a nucleic acid encoding a ligand-controllable receptor operatively associated with the FSHβ promoter, wherein the receptor binds to the response element in the presence of the ligand when expressed in a host cell, though elements (c), (d), and (e) could optionally be provided on a separate, second nucleic acid which is co-transfected along with a first nucleic acid comprising elements (a) and (b) into a common host cell.

A further aspect of the present invention is a host cell containing the recombinant nucleic acid described immediately above.

A still further aspect of the present invention is a method of making a non-human transgenic animal, comprising the steps of: (a) providing a recombinant nucleic acid as described above (i.e., one containing elements a-e as described above, separately or together as described above); (b) introducing the nucleic acid construct into a mammalian oocyte or other suitable embryonic cell; (c) implanting the oocyte embryonic cell in a suitable host such as a pseudopregnant female host; and then (d) raising the transgenic animal to viability from the oocyte or other suitable embryonic cell in the host; wherein the animal produces greater levels of FSHβ and greater numbers of gametes when administered the ligand than when not administered the ligand.

A further aspect of the present invention is a transgenic non-human animal, the animal comprising cells that contain: (a) a response element; (b) a nucleic acid encoding FSHβ operatively associated with the response element. (c) an FSHβ promoter; (d) an FSHβ locus control region operatively associated with the FSHβ promoter; and (e) a nucleic acid encoding a ligand-controllable receptor operatively associated with the FSHβ promoter, wherein the receptor binds to the response element in the presence of the ligand when expressed in a host cell; and wherein the animal produces greater levels of FSHβ and greater numbers of gametes when administered said ligand than when not administered said ligand.

A still further aspect of the present invention is a method of enhancing the production of gametes in a transgenic non-human animal, comprising the steps of: (a) providing a transgenic non-human animal selected from the group consisting of mice, sheep pigs or cows, the animal comprising cells that contain: (i) a response element; (ii) a nucleic acid encoding FSHβ operatively associated with the response element; (iii) an FSHβ promoter; (iv) an FSHβ locus control region operatively associated with the FSHβ promoter; and (v) a nucleic acid encoding a ligand-controllable receptor operatively associated with the FSHβ promoter, wherein the receptor binds to the response element in the presence of the ligand when expressed in a host cell; (b) administering the ligand to the animal mouse or pig in an amount effective to (i) stimulate the production of FSHβ in the animal above that found in a corresponding untransformed type mouse or pig; and (ii) stimulate the production of gametes in the animal to a level greater than that found in the corresponding untransformed animal. The animal may be a male and the gametes are sperm; the animal may be a female and the gametes oocytes. The gametes may be harvested from the animal, or, in the case of females, the method may further comprise the step of (c) mating the animal to produce a litter of offspring therefrom, the size of the litter being greater than the size of a litter produced by the corresponding untransformed animal the administering step may be carried out by any suitable technique, such as feeding the ligand to the animal or parenterally injecting the ligand into the animal.

Gilts in the USA normally ovulate 12-15 oocytes and give birth to ~10 piglets per pregnancy (Nat. Agric. Stat. Service, 2001). The present invention provided increased ovulation in pigs which can lead directly to increased birthing of piglets and can also be used to selectively breed for even larger litters. Meishan pigs, for instance, have higher ovulation rates and produce 20-30 piglets/litter. There are 6 million breeding sows in the USA with ~2.5 litters/year. Since $10 is gained for each "extra" piglet, $450 million/y would be gained if litter size increased by just 3 piglets. There are 4.8 million breeding ewes in the USA. If each produced 2.5 lambs instead of 1.5, and if $10 is added for the extra lamb, $48 million/yr would be gained. Spermatogenesis is often limiting in pig production. Increased sperm production (2×) would increase profits by ~$10 million/yr (estimate by W. Flowers, Animal Sciences, NCSU). Benefits can also be calculated in terms of smaller breeding herds and less waste.

The total increase in value from pig and lamb production could reasonably be $508 million/y. If savings from the transgenic industry (see below) are included, overall gains could be >$600 million annually.

Transgenic mouse facilities are found at many universities in the USA (>200). There are also >20 transgenic facilities specializing in pigs, cattle and/or sheep. Eliminating fertility drugs ($5/mouse), decreasing personnel costs and knowing that every animal will yield superovulated oocytes will cut transgenic costs considerably. A problem for transgenic facilities is the timing of fertility drug treatment. Use of the present invention will enhance proper timing. If the switch increases ovulation >2.4-fold, oocyte production can be achieved even more efficiently. Such an increase would create major benefits for the transgenic/cloning industry.

The present invention is explained in greater detail in the drawings herein and the specification below.

DETAILED DESCRIPTION OF THE PREFERRED EMBODIMENTS

Figure 1:
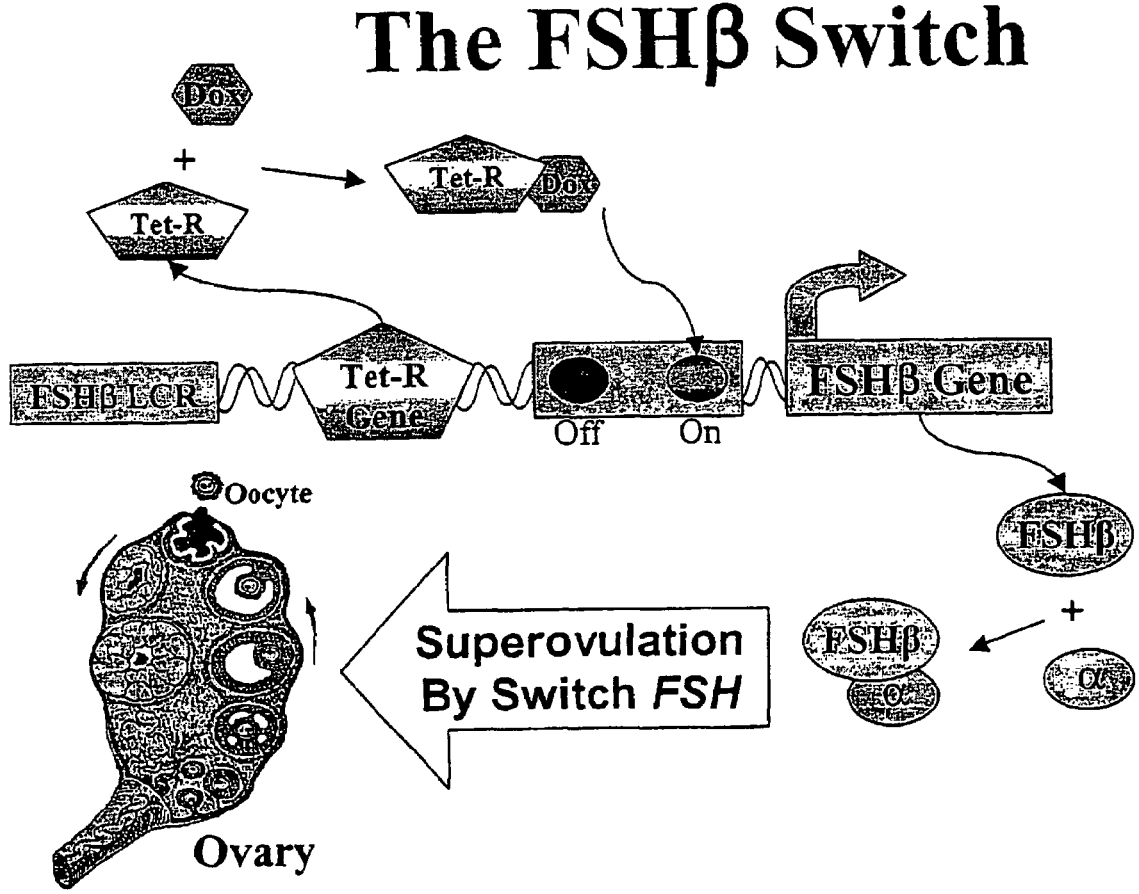
FIG. 1 schematically illustrates an embodiment of the invention in which the FSHβ switch (β-tetO DNA construct) is controlled by the ovine FSHβ promoter which expresses it ONLY in pituitary gonadotropes. It is not expressed anywhere else in the body. When doxycycline (Dox) is present, it turns on expression of the ovine FSHβ subunit which joins with excess alpha subunit in gonadotropes to make FSH. The "extra" FSH stimulates the ovary to ovulate more oocytes than normal.

"Animal" as used herein refers to higher animals such as mammals and birds. Animals include both males and females, which genders are sometimes specified as such herein.

"Mammal" as used herein refers to non-human mammals such as mice, sheep, pigs, rats, and cows.

"Bird" as used herein includes but is not limited to chickens, turkeys, ducks, geese, quail, pheasant, ostrich, emu, whooping cranes, etc.

"Operatively associated" or "operatively linked" as used herein with respect to nucleic acids indicates that the two segments of a nucleic acid functionally interact with one another in their intended manner in a host cell. For example, a promoter is operatively associated with a nucleic acid of interest when it facilitates or permits the transcription of the nucleic acid in a host cell; a locus control region is operatively associated with a promoter when it enhances the activity of the promoter to provide high level nucleic acid transcription in specific tissues (i.e., tissue-specific expression of the associated nucleic acid)

"tet operator" as used herein is intended to encompass all classes of tet operators (e.g., A, B, C, D, and E). A nucleotide sequence to be transcribed can be operatively linked to a single tet operator sequence, or for an enhanced range of regulation it can be operatively linked to multiple tet operator sequences (e.g., two, three, four, five, six, seven, eight, nine or ten or more operator sequences).

"Response element" as used herein may refer to any suitable response element such as a tet operator that activates transcription of an operatively associated nucleic acid when a ligand controllable receptor binds thereto.

"Ligand controllable receptor" as used herein refers to any transactivator protein that activates transcription in a corresponding response element when a ligand binds to that receptor and the ligand-receptor complex in turn binds to the response element. One example is a tetracycline-controllable transactivator fusion protein.

"Promoter" as used herein refers to any type of promoter, including constitutive promoters or regulated promoters, unless otherwise specified.

"FSH" as used herein refers to follicle stimulating hormone, particularly mammalian follicle stimulating hormone such as sheep, cow, mouse, pig or human follicle stimulating hormone. FSHα refers to the corresponding alpha chain thereof, and FSHβ refers to the corresponding beta chain thereof.

"Locus control region" as used herein refers to any type of locus control region adapted for high level performance of a promoter in a specific cell type or selected cell types.

"FSHβ locus control region" as used herein refers to a locus control region such as a mammalian locus control region which selectively enhances or facilitates the transcription (and potentially translation and expression) of a nucleic acid associated to it and a promoter in pituitary gonadotrope cells.

"Host cell" as used herein refers to any type of cell into which a recombinant or heterologous nucleic acid as described herein has been inserted. Such cells are generally eukaryotic cells, particularly mammalian cells, including pig, cow, sheep, and mouse cells. The cells may be of any suitable tissue type, including gametes (sperm, oocytes), stem or progenitor cells, pituitary cells such as gonadotropes, etc. In some embodiments the host cell is preferably one that also co-expresses native FSHα so that the heterologous FSHβ introduced by the present invention may be assembled into complete FSH.

A nucleic acid of interest as described herein may be any heterologous nucleic acid which it is desired to introduce into a host cell under the control of regulatory elements as described herein. The nucleic acid of interest may encode a protein or peptide, including detectable or marker proteins or peptides such as luciferase. In other embodiments, the nucleic acid of interest may encode a ligand controllable receptor, or a response element such as a tet operator.

Applicants specifically intend that all United States patent references cited herein be incorporated by reference herein in their entirety.

1. FSHβ Locus Control Regions.

As noted above, the present invention provides nucleic acids that are locus control regions, and particularly FSHβ locus control regions. For example, the nucleic acid may be:

(a) an isolated nucleic acid having the sequence given in SEQ ID NO:1 herein and encoding a sheep FSHβ locus control region (LCR), (b) an isolated nucleic acid having the sequence given SEQ ID NO:3 herein and encoding a pig FSHβ LCR, (c) an isolated nucleic acid having the sequence given in SEQ ID NO: 5 herein and encoding a human FSHβ LCR; or (d) isolated nucleic acids at least 70%, 75%, 80%, 85%, 90%, or 95% homologous or identical to the isolated nucleic acid of (a), (b) or (c) above and encoding an FSHβ locus control region, or isolated nucleic acids which hybridize to the isolated nucleic acids of (a), (b) or (c) above and encode an FSHβ locus control region. Such nucleic acids can be of any suitable origin, such as from other mammalian species, other mammalian strains or lines of the same species, or even other members of the same strain or line of animals (to thereby include natural allelic variants thereof). Such nucleic acids may be of any suitable length, such as 600, 800 or 900 nucleotides in length up to about 1100, 1200 or 1500 nucleotides in length, over which the amount or degree of homology or identity may be determined, with regions of low homology being ignored as discussed below.

Percent identity or percent homology can be determined by any suitable technique, such as BLAST analysis as described in Altschul et al., *J. Mol. Biol.* 215, 403-410, (1990) and Karlin et al., *Proc. Natl. Acad. Sci. USA* 90, 5873-5787 (1993). One useful BLAST program is the WU-BLAST-2 program, available obtained from Altschul et al., *Methods in Enzymology*, 266, 460-480 (1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. *Nucleic Acids Res.* 25, 3389-3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

Mammalian LCRs appear in many species to be divided into three subunits (each, for example, of about 100 or 150 to 250 or 300 nucleotides in length) of high homology between species, which subunits are separated by regions of low homology (each, for example, of about 100 or 150 to 250 to 300 nucleotides in length) between species. In determining the percent homology or percent identity the regions of high homology may be utilized and the regions of low homology ignored.

As an alternative approach or in addition to identifying additional LCRs by percent homology, additional LCRs can be identified based upon their ability to hybridize to known LCRs, particularly under stringent wash conditions. Conditions which will permit other polynucleotides that code on expression for a protein of the present invention to hybridize to the DNA of SEQ ID NO:1 or SEQ ID NO: 3 or SEQ ID NO: 5 disclosed herein can be determined in accordance with known techniques. For example, hybridization of such sequences may be carried out under conditions of reduced stringency, medium stringency or even stringent conditions (e.g., conditions represented by a wash stringency of 35-40% Formamide with 5× Denhardt's solution, 0.5% SDS and 1×SSPE at 37° C.; conditions represented by a wash stringency of 40-45% Formamide with 5× Denhardt's solution, 0.5% SDS, and 1×SSPE at 42° C.; and conditions represented by a wash stringency of 50% Formamide with 5× Denhardt's solution, 0.5% SDS and 1×SSPE at 42° C., respectively) to DNA of SEQ ID NO:1 or SEQ ID NO: 3 or SEQ ID NO: 5 disclosed herein in a standard hybridization assay. See, e.g., J. Sambrook et al., *Molecular Cloning, A Laboratory Manual* (2d Ed. 1989) (Cold Spring Harbor Laboratory).

2. Nucleic Acid Constructs and Transformed Host Cells.

The production of recombinant nucleic acids, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. (Applicant specifically intends that the disclosure of all patent references cited herein be incorporated herein in their entirety by reference).

As noted above, a further aspect of the present invention is an isolated nucleic acid construct comprising at least one locus control region as described above operatively associated with a promoter. The promoter may be a heterologous promoter or homologous promoter, and where a homologous promoter the isolated nucleic acid may or may not include intervening segments. Examples of LCRs associated with their corresponding homologous promoter are given in SEQ ID NO: 2, SEQ ID NO: 4, and SEQ ID NO: 6 herein. Intervening segments between the 5' LCRs and the proximal promoters could optionally be deleted. The promoter may be positioned 3' or 5' to the locus control region (perhaps due to the tendency of some nucleic acids to be inserted in tandem copies, whereby an LCR that is 3' on one insert will be 5' as to its adjacent insert). A nucleic acid of interest may be coupled to and operatively associated with the promoter, particularly to carry out some of the methods described herein.

A vector is a replicable nucleic acid construct or a nucleic acid construct used to insert particular nucleic acid constructs into a host cell. Vectors are used herein either to amplify nucleic acid constructs of the present invention or insert the constructs into a host cell or animal. Vectors comprise plasmids, viruses (e.g., adenovirus, cytomegalovirus), phage, retroviruses and linear nucleic acids such as integratable DNA fragments (i.e., fragments integratable into the host genome by recombination). The vector may replicate and function independently of the host genome or may in some instances, integrate into the genome itself.

If desired, the vector may optionally contain flanking nucleic sequences which direct site-specific homologous recombination. The use of flanking DNA sequence to permit homologous recombination into a desired genetic locus is known in the art. At present it is preferred that up to several kilobases or more of flanking DNA corresponding to the chromosomal insertion site be present in the vector on both sides of the tTA-encoding sequence (or any other sequence of this invention to be inserted into a chromosomal location by homologous recombination) to assure precise replacement of chromosomal sequences with the exogenous DNA. See e.g. Deng et al, 1993, Mol. Cell. Biol 13(4):2134-40; Deng et al, 1992, Mol Cell Biol 12(8):3365-71; and Thomas et al, 1992, Mol Cell Biol 12(7):2919-23. It should also be noted that the cell of this invention may contain multiple copies of the gene of interest, e.g. by conventional genetic amplification, each operably linked to the tTA-responsive promoter.

Transformed host cells are cells which have been transformed or transfected with vectors containing nucleic acid constructs of the invention and may or may not transcribe or translate the operatively associated nucleic acid of interest.

3. Response Elements and Genetic Switches Employing the Same.

Response elements are known and any suitable response element may be employed in carrying out the present invention.

In one particular embodiment, as described in U.S. Pat. No. 5,866,755 to Bujard et al. (BASF) and discussed in greater detail below, the response element is a tet operator; the ligand-controllable receptor is a tetracycline-controllable transactivator fusion protein; and the ligand is tetracycline or an analog thereof such as doxycycline.

Tetracycline-Inducible Transcriptional Activators. In the inducible regulatory used in the present invention, transcription of a nucleic acid of interested is activated by a transcriptional activator protein, also referred to herein simply as a transactivator. The transactivator of the invention may be a fusion protein. The term "fusion protein" is intended to describe at least two polypeptides, typically from different sources, which are operatively linked. With regard to the polypeptides, the term "operatively linked" is intended to mean that the two polypeptides are connected in manner such that each polypeptide can serve its intended function. Typically, the two polypeptides are covalently attached through peptide bonds. The fusion protein is preferably produced by standard recombinant DNA techniques. For example, a DNA molecule encoding the first polypeptide is ligated to another DNA molecule encoding the second polypeptide, and the resultant hybrid DNA molecule is expressed in a host cell to produce the fusion protein. The DNA molecules are ligated to each other in a 5' to 3' orientation such that, after ligation, the translational frame of the encoded polypeptides is not altered (i.e., the DNA molecules are ligated to each other in-frame).

A. The first polypeptide of the transactivator fusion protein. The transactivator fusion protein may be composed, in part, of a first polypeptide which binds to a tet operator sequence in the presence of tetracycline (Tc), or an analog thereof. The first polypeptide of the fusion protein is preferably a mutated Tet repressor. The term "mutated Tet repressor" is intended to include polypeptides having an amino acid sequence which is similar to a wild-type Tet repressor but which has at least one amino acid difference from the wild-type Tet repressor. The term "wild-type Tet repressor" is intended to describe a protein occurring in nature which represses transcription from tet operator sequences in prokaryotic cells in the absence of Tc. The amino acid difference(s) between a mutated Tet repressor and a wild-type Tet repressor may be substitution of one or more amino acids, deletion of one or more amino acids or addition of one or more amino acids. The mutated Tet repressor of the invention has the following functional properties: 1) the polypeptide can bind to a tet operator sequence, i.e., it retains the DNA binding specificity of a wild-type Tet repressor; and 2) it is regulated in a reverse manner by tetracycline than a wild-type Tet repressor, i.e., the mutated Tet repressor binds to a tet operator sequence only the presence of Tc (or Tc analogue) rather than in the absence of Tc.

In one embodiment, a mutated Tet repressor having the functional properties described above is created by substitution of amino acid residues in the sequence of a wild-type Tet repressor. For example, as described in Example 1 of U.S. Pat. No. 5,866,755, a Tn10-derived Tet repressor having amino acid substitutions at amino acid positions 71, 95, 101 and 102 has the desired functional properties and thus can be used as the first polypeptide in the transactivator fusion protein of the invention. The amino acid sequence of this mutated Tet repressor is shown in SEQ ID NO: 2 (positions 1-207) of U.S. Pat. No. 5,866,755. In one embodiment of the mutated Tet repressor, position 71 is mutated from glutamic acid to lysine, position 95 is mutated from aspartic acid to asparagine, position 101 is mutated from leucine to serine and position 102 is mutated from glycine to aspartic acid, although the invention is not limited to these particular mutations. Mutation of fewer than all four of these amino acid positions may be sufficient to achieve a Tet repressor with the desired functional properties Accordingly, a Tet repressor is preferably mutated at at least one of these positions Other amino acid substitutions, deletions or additions at these or other amino acid positions which retain the desired functional properties of the mutated Tet repressor are within the scope of the invention. The crystal structure of a Tet repressor-tetracycline complex, as described in Hinrichs, W. et al. (1994) Science 264:418-420, can be used for rational design of mutated Tet repressors. Based upon this structure, amino acid position 71 is located outside the tetracycline binding pocket, suggesting mutation at this site may not be necessary to achieve the desired functional properties of a mutated Tet repressor of the invention. In contrast, amino acid positions 95, 101 and 102 are located within the conserved tetracycline binding pocket. Thus, the tetracycline binding pocket of a Tet repressor may be targeted for mutation to create a mutated Tet repressor that may be used to carry out the present invention.

Additional mutated Tet repressors for incorporation into a fusion protein of the invention can be created according to the teachings of the invention. A number of different classes of Tet repressors have been described, e.g., A, B, C, D and E (of which the Tn10-encoded repressor is a class B repressor). The amino acid sequences of the different classes of Tet repressors share a high degree of homology (i.e., 40-60% across the length of the proteins), including in the region encompassing the above-described mutations. The amino acid sequences of various classes of Tet repressors are shown and compared in FIG. 4 of U.S. Pat. No. 5,866,755, and are also described in Tovar, K. et al. (1988) Mol. Gen. Genet. 215:76-80. Accordingly, equivalent mutations to those described above for the Tn10-derived Tet repressor can be made in other classes of Tet repressors for inclusion in a fusion protein of the invention. For example, amino acid position 95, which is an aspartic acid in all five repressor classes, can be mutated to asparagine in any class of repressor. Similarly, position 102, which is glycine in all five repressor classes, can be mutated to aspartic acid in any class of repressor. Additional suitable equivalent mutations will be apparent to those skilled in the art and can be created and tested for functionality by procedures described herein. Nucleotide and amino acid sequences of Tet repressors of the A, C, D and E classes are disclosed in Waters, S. H. et al. (1983) Nucl. Acids Res 11:6089-6105, Unger, B. et al. (1984) Gene 31: 103-108, Unger, B. et al. (1984) Nucl Acids Res. 12:7693-7703 and Tovar, K. et al. (1988) Mol. Gen. Genet. 215:76-80, respectively. These wild-type sequences can be mutated according to the teachings of U.S. Pat. No. 5,866,755 for use in the inducible regulatory system described herein.

Alternative to the above-described mutations, additional suitable mutated Tet repressors (i.e., having the desired functional properties described above) can be created by mutagenesis of a wild type Tet repressor and selection as described in Example 1 of U.S. Pat. No. 5,866,755. The nucleotide and amino acid sequences of wild-type class B Tet repressors are disclosed in Hillen, W. and Schollmeier, K. (1983) Nucl. Acids Res. 11:525-539 and Postle, K. et al. (1984) Nucl. Acids Res. 12:4849-4863. The nucleotide and amino acid sequences of wild-type class A, C, D and E type repressors are cited above. A mutated Tet repressor can be created and selected, for example as follows: a nucleic acid (e.g., DNA) encoding a wild-type Tet repressor is subjected to random mutagenesis and the resultant mutated nucleic acids are incorporated into an expression vector and introduced into a host cell for screening. A screening assay is used which allows for selection of a Tet repressor which binds to a tet operator sequence only in the presence of tetracycline. For example, a library of mutated nucleic acids in an expression vector can be introduced into an E. coli strain in which tet operator sequences control the expression of a gene encoding a Lac repressor and the Lac repressor controls the expression of a gene encoding an selectable marker (e.g., drug resistance). Binding of a Tet repressor to tet operator sequences in the bacteria will inhibit expression of the Lac repressor, thereby inducing expression of the selectable marker gene. Cells expressing the marker gene are selected based upon the selectable phenotype (e.g., drug resistance). For wild-type Tet repressors, expression of the selectable marker gene will occur in the absence of Tc. A nucleic acid encoding a mutated Tet repressor is selected using this system based upon the ability of the nucleic acid to induce expression of the selectable marker gene in the bacteria only in the presence of Tc.

A first polypeptide of the transactivator fusion protein (e.g., the mutated Tet repressor) has the property of binding specifically to a tet operator sequence. Each class of Tet repressor has a corresponding target tet operator sequence. Accordingly, the term "tet operator sequence" is intended to encompass all classes of tet operator sequences, e.g. class A, B, C, D, and E. Nucleotide sequences of these five classes of tet operators are shown in FIG. 5 and SEQ ID NOs: 11-15 of U.S. Pat. No. 5,866,755, and are described in Waters, S. H. et al. (1983) cited supra, Hillen, W. and Schollenmeier, K. (1983) cited supra, Stuber, D. and Bujard, H. (1981) Proc. Natl. Acad. Sci. USA 78:167-171, Unger, B. et al. (1984) cited supra and Tovar, K. et al. (1988). In one embodiment, the mutated Tet repressor is a Tn10-encoded repressor (i.e., class B) and the let operator sequence is a class B let operator sequence. Alternatively, a mutated class A Tet repressor can be used with a class A let operator sequence, and so on for the other classes of Tet repressor/operators.

Another approach for creating a mutated Tet repressor which binds to a class A tet operator is to further mutate the already mutated Tn10-derived Tet repressor described herein (a class B repressor) such that it no longer binds efficiently to a class B type operator but instead binds efficiently to a class A type operator. It has been found that nucleotide position 6 of class A or B type operators is the critical nucleotide for recognition of the operator by its complimentary repressor (position 6 is a G/C pair in class B operators and an A/T pair in class A operators) (see Wissman et al. (1988) J Mol. Biol. 202:397-406). It has also been found that amino acid position 40 of a class A or class B Tet repressor is the critical amino acid residue for recognition of position 6 of the operator (amino acid position 40 is a threonine in class B repressors but is an alanine in class A repressors). It still further has been found that substitution of Thr40 of a class B repressor with Ala alters its binding specificity such that the repressor can now bind a class A operator (similarly, substitution of Ala40 of a class A repressor with Thr alters its binding specificity such that the repressor can now bind a class B operator) (see Altschmied et al. (1988) EMBO J. 7:4011-4017). Accordingly, one can alter the binding specificity of the mutated Tn10-derived Tet repressor by additionally changing amino acid residue 40 from Thr to Ala by standard molecular biology techniques (e.g., site directed mutagenesis).

A mutated Tet repressor having specific mutations (e.g., at positions 71, 95, 101 and/or 102, as described above) can be created by introducing nucleotide changes into a nucleic acid encoding a wild-type repressor by standard molecular biology techniques, e.g. site directed mutagenesis or PCR-mediated mutagenesis using oligonucleotide primers incorporating the nucleotide mutations. Alternatively, when a mutated Tet repressor is identified by selection from a library, the mutated nucleic acid can be recovered from the library vector. To create a transactivator fusion protein of the invention, a nucleic acid encoding a mutated Tet repressor is then ligated in-frame to another nucleic acid encoding a transcriptional activation domain and the fusion construct is incorporated into a recombinant expression vector.

B. The second polypeptide of the transactivator fusion protein. The first polypeptide of the transactivator fusion protein is operatively linked to a second polypeptide which directly or indirectly activates transcription in eukaryotic cells. To operatively link the first and second polypeptides, typically nucleotide sequences encoding the first and second polypeptides are ligated to each other in-frame to create a chimeric gene encoding a fusion protein, although the first and second polypeptides can be operatively linked by other means that preserve the function of each polypeptide (e.g., chemically crosslinked). In one embodiment, the second polypeptide of the transactivator itself possesses transcriptional activation activity (i.e., the second polypeptide directly activates transcription). In another embodiment, the second polypeptide activates transcription by an indirect mechanism, through recruitment of a transcriptional activation protein to interact with the fusion protein. Accordingly, the term "a polypeptide which activates transcription in eukaryotic cells" as used herein is intended to include polypeptides which either directly or indirectly activates transcription.

Polypeptides which can function to activate transcription in eukaryotic cells are well known in the art. In particular, transcriptional activation domains of many DNA binding proteins have been described and have been shown to retain their activation function when the domain is transferred to a heterologous protein. A preferred polypeptide for use in the fusion protein of the invention is the herpes simplex virus virion protein 16 (referred to herein as VP16, the amino acid sequence of which is disclosed in Triezenberg, S. J. et al. (1988) Genes Dev. 2:718-729). In one embodiment, about 127 of the C-terminal amino acids of VP16 are used. For example, a polypeptide having an amino acid sequence shown in SEQ ID NO: 2 (positions 208-335) of U.S. Pat. No. 5,866,755 can be used as the second polypeptide in the fusion protein. In another embodiment, at least one copy of about 11 amino acids from the C-terminal region of VP16 which retain transcriptional activation ability is used as the second polypeptide. Preferably, a dimer of this region (i.e., about 22 amino acids) is used. Suitable C-terminal peptide portions of VP16 are described in Seipel, K. et al. (EMBO J. (1992) 13:4961-4968). For example, a dimer of a peptide having an amino acid sequence shown in SEQ ID NO: 4 (encoded by a nucleotide sequence shown in SEQ ID NO: 3) of U.S. Pat. No. 5,866,755 can be used as the second polypeptide in the fusion protein.

Other polypeptides with transcriptional activation ability in eukaryotic cells can be used in the fusion protein of the invention. Transcriptional activation domains found within various proteins have been grouped into categories based upon similar structural features. Types of transcriptional activation domains include acidic transcription activation domains, proline-rich transcription activation domains, serine/threonine-rich transcription activation domains and glutamine-rich transcription activation domains. Examples of acidic transcriptional activation domains include the VP16 regions already described and amino acid residues 753-881 of GAL4. Examples of proline-rich activation domains include amino acid residues 399-499 of CTF/NF1 and amino acid residues 31-76 of AP2. Examples of serine/threonine-rich transcription activation domains include amino acid residues 1-427 of ITF1 and amino acid residues 2-451 of ITF2. Examples of glutamine-rich activation domains include amino acid residues 175-269 of Oct1 and amino acid residues 132-243 of Sp1. The amino acid sequences of each of the above described regions, and of other useful transcriptional activation domains, are disclosed in Seipel, K. et al. (EMBO J. (1992) 13:4961-4968).

In addition to previously described transcriptional activation domains, novel transcriptional activation domains, which can be identified by standard techniques, are within the scope of the invention. The transcriptional activation ability of a polypeptide can be assayed by linking the polypeptide to another polypeptide having DNA binding activity and determining the amount of transcription of a target sequence that is stimulated by the fusion protein. For example, a standard assay used in the art utilizes a fusion protein of a putative transcriptional activation domain and a GAL4 DNA binding domain (e.g., amino acid residues 1-93). This fusion protein is then used to stimulate expression of a reporter gene linked to GAL4 binding sites (see e.g., Seipel, K. et al. (1992) EMBO J. 11:4961-4968 and references cited therein).

In another embodiment, the second polypeptide of the fusion protein indirectly activates transcription by recruiting a transcriptional activator to interact with the fusion protein. For example, a mutated tetR of the invention can be fused to a polypeptide domain (e.g., a dimerization domain) capable of mediating a protein-protein interaction with a transcriptional activator protein, such as an endogenous activator present in a host cell. It has been demonstrated that functional associations between DNA binding domains and transactivation domains need not be covalent (see e.g., Fields and Song (1989) Nature 340:245-247; Chien et al. (1991) Proc. Natl. Acad. Sci. USA 88:9578-9582; Gyuris et al. (1993) Cell 75:791-803; and Zervos, A. S. (1993) Cell 72:223-232). Accordingly, the second polypeptide of the fusion protein may not directly activate transcription but rather may form a stable interaction with an endogenous polypeptide bearing a compatible protein-protein interaction domain and transactivation domain. Examples of suitable interaction (or dimerization) domains include leucine zippers (Landschulz et al. (1989) Science 243:1681-1688), helix-loop-helix domains (Murre, C. et al. (1989) Cell 58:537-544) and zinc finger domains (Frankel, A. D. et al. (1988) Science 240:70-73). Interaction of a dimerization domain present in the fusion protein with an endogenous nuclear factor results in recruitment of the transactivation domain of the nuclear factor to the fusion protein, and thereby to a tet operator sequence to which the fusion protein is bound.

C. A third polypeptide of the transactivator fusion protein. In addition to a mutated Tet repressor and a transcriptional activation domain, a fusion protein of the invention can contain an operatively linked third polypeptide which promotes transport of the fusion protein to a cell nucleus. Amino acid sequences which, when included in a protein, function to promote transport of the protein to the nucleus are known in the art and are termed nuclear localization signals (NLS). Nuclear localization signals typically are composed of a stretch of basic amino acids. When attached to a heterologous protein (e.g., a fusion protein of the invention), the nuclear localization signal promotes transport of the protein to a cell nucleus. The nuclear localization signal is attached to a heterologous protein such that it is exposed on the protein surface and does not interfere with the function of the protein. Preferably, the NLS is attached to one end of the protein, e.g. the N-terminus. The amino acid sequence of a non-limiting example of an NLS that can be included in a fusion protein of the invention is shown in SEQ ID NO: 5 of U.S. Pat. No. 5,866,755. Preferably, a nucleic acid encoding the nuclear localization signal is spliced by standard recombinant DNA techniques in-frame to the nucleic acid encoding the fusion protein (e.g., at the 5' end).

The second component of the genetic switch is the tTA-responsive transcriptional promoter to which the gene of interest is operably linked. The promoter may be a minimal promoter comprising, for example, a portion of the cytomegalovirus (CMV) IE promoter, operably linked to at least one tet operator sequence, derived for example from the tetracycline resistance operon encoded in Tn10 of *E. coli* (Hillen & Wissmann, "Topics in Molecular and Structural biology" in Protein-Nucleic Acid Interaction, Saeger & Heinemannn eds., Macmillan, London, 1989, Vol. 10, pp. 143-162), to serve as target sequences for a tTA. Other suitable minimal promoters include PhCMV*-1, PhCMV*-2, and PtK*-1, or other minimal promoters derived from promoter elements typically used in the cell line employed as described in the references throughout this application. Minimal promoter elements particularly useful for a given cell line may be selected from a series of deletion mutants of the original promoter nucleotide sequence, based on the ability of a given member of the series (for instance, placed as a XhoI/Sacl1 fragment into the corresponding restriction sites of plasmid pUHC13-3) to be activated in transient transfection experiments using a cell line stably expressing the tetR-VP16 fusion protein; as will be appreciated a cell line stably expressing any other fusion of tetR with a protein domain capable of activating transcription (see below) can be used. As will also be appreciated plasmid pUHC13-3 may be modified for the specific application by replacing genetic elements like polyadenylation sites or splice sites with those functioning in the cell line in question. Specific details may be found in the references throughout this application or references cited therein, the full contents of which are incorporated herein by reference. A second criterion for the selection of the optimal minimal promoter is the degree of repression in the presence of tetracycline.

Tetracycline analog ligands. A "tetracycline analog" is any one of a number of compounds that are closely related to tetracycline (Tc) and which bind to the tet repressor with a Ka of at least about $10^6$ $M^{-1}$. Examples of such tetracycline analogues include, but are not limited to those disclosed by Hlavka and Boothe, "The Tetracyclines," in Handbook of Experimental Pharmacology 78, R. K. Blackwood et al. (eds.), SpringerVerlag, Berlin-N.Y., 1985; L. A. Mitscher "The Chemistry of the Tetracycline Antibiotics, Medicinal Research 9, Dekker, N.Y., 1978; Noyee Development Corporation, "Tetracycline Manufacturing Processes," Chemical Process Reviews, Park Ridge, N.J., 2 volumes, 1969; R. C. Evans, "The Technology of the Tetracyclines," Biochemical Reference Series 1, Quadrangle Press, New York, 1968; and H. F. Dowling, "Tetracycline," Antibiotics Monographs, no. 3, Medical Encyclopedia, New York, 1955; the contents of each of which are fully incorporated by reference herein. Examples of tetracycline analogues include anhydrotetracycline, doxycycline, chlorotetracycline, epioxytetracycline, cyanotetracycline and the like. Certain Tc analogues, such as anhydrotetracycline and epioxytetracycline, have reduced antibiotic activity compared to Tc.

Steroid response elements function in like manner to the tet operator-based response element and can also be utilized herein. Thus, in another embodiment, the response element is a progesterone receptor response element; the ligand-controllable receptor is a progesterone-controllable transactivator protein; and the ligand is progesterone or an analog thereof. In still another embodiment, the response element is an estrogen receptor response element; the ligand-controllable receptor is an estrogen-controllable transactivator protein; and the ligand is estrogen or an analog thereof.

4. Transgenic Animals and Methods of Making.

The production of transgenic animals is well known. For example, U.S. Pat. No. 5,859,310 to Bujard et al., at column 17, generally describes methods in which a transgenic animal which contains in it's genome the nucleic acid of interest is produced by the following steps: (1) A chimeric DNA sequence is prepared where a Tc responsive promoter element, (comprising at least one tet operator and a minimal promoter) is cloned 5' of the DNA sequences encoding the endogenous gene of interest. (2) The chimeric DNA sequence (called also "the chimeric transgene") is then injected into a fertilized egg, which is implanted into a pseudopregnant recipient mother and allowed to develop into an adult animal. In particular, a few hundred DNA molecules are injected into the pro-nucleus of a fertilized one cell egg. The microinjected eggs are then transferred into the oviducts of pseudopregnant foster mothers and allowed to develop. See generally Brinster et al. Proc. Natl. Acad. Sci. U.S.A. Vol. 83:9065-9069 (1986). Breeding of animals resulting from this process produces offspring containing the chimeric transgene. As will be appreciated, the particular breeding strategy depends on factors such as the nucleic acid of interest and the animal into which it is inserted. Animals of the present invention can be produced by substantially the same techniques, by injecting nucleic acid constructs of the present invention.

U.S. Pat. No. 4,873,191 to Wagner and Hoppe (Ohio University) describes a method of obtaining a mammal characterized as having a plurality of cells containing exogenous genetic material, the material including at least one gene and a control sequence operably associated therewith, which, under predetermined conditions, express the gene under the control of the control sequence in a cell of the mammal. The method comprises: (a) introducing exogenous genetic material into a pronucleus of a mammalian zygote by microinjection, the zygote being capable of development into a mammal, the genetic material including at least one gene and a control sequence operably associated therewith, thereby obtaining a genetically transformed zygote; (b) transplanting an embryo derived from the genetically transformed zygote into a pseudopregnant female capable of bearing the embryo to term; and (c) allowing the embryo to develop to term; where the gene and control sequence are selected so that the gene is not activated in such manner and degree as would prevent normal development of the embryo to term. Again, animals of the present invention can be produced by substantially the same techniques, by introducing nucleic acid constructs of the present invention into the pronucleus zygote by microinjection.

U.S. Pat. No. 4,736,866 to Leder and Stewart (Harvard) describes a transgenic non-human mammal and methods of making the same, wherein mammal all of the germ cells and somatic cells of the transgenic animal contain a recombinant activated oncogene sequence introduced into the mammal, or an ancestor of the mammal, at an embryonic stage. Animals of the present invention can be made by like techniques by introduction of nucleic acid constructs as described herein. Note also that the present invention is useful for propagating transgenic animal models of disease, such as those described in Leder and Stewart, where it is desirable to increase the size of the litter of the breeding animals.

U.S. Pat. No. 4,873,316 to Meade and Lonberg (Biogen) describes a process for the production and secretion into mammal's milk of an exogenous recombinate protein comprising the steps of: (a) producing milk in a transgenic mammal characterized by an expression system comprising a casein promoter operatively linked to an exogenous DNA sequence coding for the recombinant protein through a DNA sequence coding for a signal peptide effective in secreting and maturing the recombinant protein in mammary tissue; (b) collecting the milk; and (c) isolating the exogenous recombinant protein from the milk. Animals of the present invention can be produced by like techniques as described therein In addition, animals as described in Meade and Lonberg, further comprising cells containing nucleic acid constructs of the present invention as described herein, are a further embodiment of the present invention.

U.S. Pat. No. 6,369,294 to J. Piedrahata and F. Bazer (Texas A&M University System) describes a method of producing a transgenic pig comprising (a) introducing a selected DNA segment into a cell culture comprising porcine primordial germ cells to obtain candidate porcine primordial germ cells that contain the selected DNA segment; (b) plating the candidate porcine primordial germ cells that contain the selected DNA segment on feeder cells (the feeder cells preferably at a density of between about $2.5 \times 10^5$ cells/cm$^2$ and about $10^6$ cells/m$^2$), in a culture medium comprising an effective amount of basic fibroblast growth factor and an apoptosis inhibitor, to obtain undifferentiated porcine primordial germ cells that contain the selected DNA segment; and (c) generating a transgenic pig from the undifferentiated porcine primordial germ cells that contain the selected DNA segment, wherein the selected DNA segment is contained and expressed in somatic and germ cells of the transgenic pig. Animals of the present invention can be produced in like manner by utilizing the nucleic acid constructs described herein as the selected DNA segment.

U.S. Pat. No. 6,344,596 to W. Velander et al. (American Red Cross) describes a non-human transgenic mammal containing an exogenous DNA molecule that is stably integrated in its genome, wherein the exogenous DNA molecule comprises: (a) 5' regulatory sequences of a mammary gland-specific gene including a promoter; (b) a Factor IX-encoding DNA sequence that encodes a signal sequence, a Factor IX pro-sequence, and a Factor IX sequence in a 5' to 3' direction, wherein the signal sequence is effective in directing the secretion of the Factor IX into the milk of the transgenic mammal and wherein the Factor IX sequence lacks the complete 5'-untranslated and 3'-untranslated regions of the Factor IX gene; and (c) 3' regulatory sequences from a mammary gland-specific gene or 3' regulatory sequences active in a mammary gland, wherein the 5' and the 3' regulatory sequences are operatively linked to the Factor IX-encoding DNA sequence, and wherein the promoter is selected from the group consisting of whey acidic protein (WAP) promoter, α-casein promoter, β-casein promoter, κ-casein promoter, α-lactalbumin promoter and β-lactoglobulin promoter. The transgenic mammal is preferably selected from the group consisting of mice, rats, rabbits, pigs, sheep, goats and cows. Animals of the present invention can be produced in like manner as described therein, and the present invention can be utilized to increase the litter size or gamete production in animals as described therein.

U.S. Pat. No. 6,339,183 to T. T. Sun (New York University) describes a nonhuman transgenic mammalian animal whose genome comprises a promoter construct linked to a heterologous DNA encoding a selected biologically active molecule, wherein the promoter construct directs expression of the heterologous DNA to the urothelium and the transgenic mammalian animal has detectable levels of the selected biologically active molecule in its urine. The mammal is preferably selected from the group consisting of mice, rats, cows, pigs, sheep, goats, monkeys, and rabbits. Animals of the present invention can be produced in like manner as described therein, and the present invention can be utilized to increase the litter size or gamete production in animals as described therein.

U.S. Pat. No. 6,331,658 to D. Cooper and E. Koren describes non-human transgenic mammals, and methods of making the same, wherein the genome of the mammal stably includes a nucleotide sequence encoding a sialyltransferase or fucosyltransferase in operable linkage with a promoter, wherein expression of the nucleotide sequence in at least some of the cells of an organ of the mammal results in a reduction of 1→3 galactosyl epitopes on the surface of at least some of the cells of the organ of the mammal such that the organ exhibits a decrease in antibody-mediated rejection when the tissue is exposed to human serum as compared to a mammalian organ of the same species which does not comprise cells expressing the nucleotide sequence. The animals are useful as a source of organs or tissue for transplant. Animals of the present invention can be produced in like manner as described therein, and the present invention can be utilized to increase the litter size or gamete production in animals as described therein.

U.S. Pat. No. 6,255,554 to H. Lubon et al. (American National Red Cross; Virginia Polytechnic Institute) describes a non-human transgenic mammal and methods of making the same, where the mammal produces in its mammary gland cells and secretes into its milk at detectable levels human Factor VIII or fragment thereof which retains physiological activity of human Factor VIII and human von Willebrand Factor or fragment thereof which retains physiological activity of human von Willebrand Factor, wherein the transgenic mammal has stably integrated into its genome a first exogenous gene construct and a second exogenous gene construct, wherein the first exogenous gene construct comprises: (a) 5' expression regulating sequences, including a mammary gland-specific promoter; (b) DNA encoding the Factor VIII or fragment thereof, and a signal sequence effective in directing secretion of the Factor VIII or fragment thereof into the milk of the transgenic mammal; and (c) 3' regulatory sequences, including a polyadenylation signal, that result in the expression of the DNA encoding the Factor VIII or fragment thereof, in the mammary gland cells, wherein (a), (b) and (c) are operably linked in the first exogenous gene construct to obtain production of the Factor VIII or fragment thereof in the mammary gland cells and secretion thereof into the milk of the transgenic mammal; and the second exogenous gene construct comprises: (d) 5' expression regulating sequences, including a mammary gland-specific promoter; (e) DNA encoding the von Willebrand Factor or fragment thereof, and a signal sequence effective in directing secretion of the von Willebrand Factor or fragment thereof into the milk of the transgenic mammal; and (f) 3' regulatory sequences, including a polyadenylation signal, that result in the expression of the DNA encoding the von Willebrand Factor or fragment thereof, in the mammary gland cells, wherein (d), (e) and (f) are operably linked in the second exogenous gene construct to obtain production of the von Willebrand Factor or fragment thereof in the mammary gland cells and secretion thereof into the milk of the transgenic mammal. The mammal is preferably a mouse, rat, rabbit, pig, sheep, goat and cattle. Animals of the present invention can be produced in like manner as described therein, and the present invention can be utilized to increase the litter size or gamete production in animals as described therein.

U.S. Pat. No. 6,204,431 to P. Prieto et al. (Abbott Laboratories) describes a non-human, transgenic mammal, wherein the genome of the mammal comprises at least one heterologous DNA sequence encoding an enzyme, wherein the enzyme is a glycosyltransferase operatively linked to a mammary gland-specific promoter, wherein expression of the at least one DNA sequence results in the production of oligosaccharides and glycoproteins in the milk of the mammal. The mammal is preferably a mouse, a rat, a rabbit, a pig, a goat, a sheep and a cow. Animals of the present invention can be produced in like manner as described therein, and the present invention can be utilized to increase the litter size or gamete production in animals as described therein.

U.S. Pat. No. 6,166,288 to L. Diamond et al. (Nextran Inc., Princeton, N.J.), describes transgenic pigs and methods of making the same which may be used in a method of preparing organs, tissues, or cells for xenotransplantation into human patients with reduced rejection comprising the steps of: (a) providing a transgenic pig which is a source of transplant material which is anatomically and physiologically compatible with a human patient, the material selected from the group consisting of organs, tissues, or cells, the pig expressing (i) at least one transgenically encoded enzyme, functional in the pig, and in particular in the organs, tissues, or cells, that masks or reduces the level of a zenoreactive antigen of the transplant material, the at least one enzyme being a fucosyltransferase, and (ii) at least one transgenically encoded complement inhibitor functional in humans; and (b) isolating the transplant material from the transgenic pig, the material having been modified by the enzyme, wherein the modification results in a masking or a reduction in the level of a zenoreactive antigen thereof, the material further being associated with the complement inhibitor. Animals of the present invention can be produced in like manner as described therein, and the present invention can be utilized to increase the litter size or gamete production in animals as described therein.

U.S. Pat. No. 5,959,171 to J. M. Hyttinin et al. (Pharming BV), describes transgenic non-human mammals and methods of making the same, where the mammal's genome comprises a mammary gland specific expression system, wherein the mammal is selected from the group consisting of mouse, rat, rabbit, sheep, pig and cow, and wherein a detectable level of erythropoietin is expressed in the milk of the transgenic mammal or a descendant of the mammal. The mammary gland specific expression system comprising in operable linkage: (a) expression regulatory elements from a milk protein gene or a mammary tumor virus, (b) a DNA sequence encoding a signal sequence, (c) a DNA sequence encoding a fragment of a non-EPO protein, where the fragment is sufficient to reduce or prevent the formation of side effects associated with ectopic expression or leakage of erythropoietin, or a DNA sequence encoding a non-EPO protein, wherein the protein reduces or prevents the formation of side effects associated with ectopic expression or leakage of erythropoietin, and a (d) a DNA sequence encoding erythropoietin, whereby elements (c) and (d) are linked in frame forming a fusion protein. Animals of the present invention can be produced in like manner as described therein, and the present invention can be utilized to increase the litter size or gamete production in animals as described therein.

U.S. Pat. No. 5,880,327 to H. Lubon et al. (American Red Cross) describes a non-human transgenic mammal that produces in its mammary gland cells and secretes into its milk at detectable levels a recombinant human Factor VIII protein or fragment or modification thereof having physiological activity of human Factor VIII, wherein the transgenic mammal has stably integrated into its genome an exogenous gene construct comprising: (a) 5' expression regulating sequences, including a mammary gland-specific promoter; (b) DNA encoding the Factor VIII protein or fragment or modification thereof, and a signal sequence effective in directing secretion of the Factor VIII protein or fragment thereof into the milk of the transgenic mammal; and (c) 3' regulatory sequences, including a polyadenylation signal, that result in the expression of the DNA in the mammary gland cells, wherein (a), (b), and (c) are operably linked in the gene construct to obtain production of the Factor VIII protein or fragment or modification thereof in the mammary gland cells and secretion thereof into the milk of the transgenic mammal. The mammal is preferably mouse, rat, rabbit, pig, sheep, goat or cattle. Animals of the present invention can be produced in like manner as described therein, and the present invention can be utilized to increase the litter size or gamete production in animals as described therein.

U.S. Pat. No. 5,639,457 to G. Brem describes a process for the production of antibodies, comprising the steps of: introducing at least one DNA sequence coding for a rearranged antibody, the DNA sequence being free of bacterial foreign sequences, into the male pronucleus of a fertilized ovum of a pig or rabbit by microinjection, implanting the ovum in the oviduct of a pig or rabbit to obtain offspring, raising the resulting transgenic animal, and isolating the rearranged antibody from the transgenic animal wherein the rearranged antibody is produced at a concentration of at least 200 µg/ml. Animals of the present invention can be produced in like manner as described therein, and the present invention can be utilized to increase the litter size or gamete production in animals as described therein.

U.S. Pat. No. 5,639,940 to I. Garner et al. (Pharmaceutical Proteins Ltd.; Zymogenetics Inc) describes a method for producing biocompetent fibrinogen comprising: providing a first DNA segment encoding a secretion signal operably linked to a heterologous fibrinogen Aα chain, a second DNA segment encoding a secretion signal operably linked to a heterologous fibrinogen Bβ chain, and a third DNA segment encoding a secretion signal operably linked to a heterologous fibrinogen γ chain, wherein each chain is from the same species, and wherein each of the first, second and third segments is operably linked to additional DNA segments required for its expression in the mammary gland of a host female mammal; introducing the DNA segments into a fertilized egg of a non-human mammalian species heterologous to the species of origin of the fibrinogen chains; inserting the egg into an oviduct or uterus of a female of the mammalian species to obtain offspring carrying the DNA segments; breeding the offspring to produce female progeny that express the first, second and third DNA segments and produce milk containing biocompetent fibrinogen encoded by the segments; collecting milk from the female progeny; and and recovering the biocompetent fibrinogen from the milk. Animals of the present invention can be produced in like manner as described therein, and the present invention can be utilized to increase the litter size or gamete production in animals as described therein.

U.S. Pat. No. 5,589,604 to W. Drohan et al. (American Red Cross) describes a transgenic non-human mammal that contains and expresses a human protein C DNA construct in the cells of its mammary gland, wherein the DNA construct consists of: (a) a mammary gland promoter, (b) a nucleotide sequence that encodes a signal peptide, wherein the signal peptide is effective in directing the secretion of an associated polypeptide into the milk of the transgenic non-human mammal, and wherein the signal peptide-encoding nucleotide sequence is operatively associated with the mammary gland promoter, and (c) a nucleotide sequence encoding human protein C that is operatively associated with the signal peptide-encoding nucleotide sequence, wherein human protein C is secreted into the milk of the transgenic non-human mammal, and when purified, the protein C has a specific activity more than about 80% of the specific activity of human protein C isolated from human plasma, as determined by an assay of protein C serine protease activity or anticoagulant activity, and wherein the non-human mammal is selected from the group consisting of mouse, pig, sheep, goat and cattle. Animals of the present invention can be produced in like manner as described therein, and the present invention can be utilized to increase the litter size or gamete production in animals as described therein.

U.S. Pat. No. 5,602,306 to Townes et al. (UAB Research Foundation) describes a transgenic pig produced by a method comprising introducing into a singlecelled pig embryo two species of recombinant nucleic acid molecule, one of which comprises at least one erythroid-specific β-globin DNase I hypersensitive site directing expression of human α-globin protein and the other of which comprises at least one erythroid-specific β-globin DNAse I hypersensitive site directing expression of human β-globin protein, whereby a transgenic pig expressing human hemoglobin is produced. Animals of the present invention can be produced in like manner as described therein, and the present invention can be utilized to increase the litter size or gamete production in animals as described therein.

U.S. Pat. No. 5,573,933 to R. Seamark and J. Wells (Luminis Pty., Ltd.) describes a method for preparing a transgenic pig which overexpresses porcine growth hormone, the method comprising the steps of: (a) obtaining a recently fertilized pig ovum; (b) isolating a first DNA sequence encoding a human metalliothionine IIA promoter; (c) inserting the first DNA sequence into a plasmid cloning vector; (d) isolating a second DNA sequence encoding porcine growth hormone, the second DNA sequence being an EcoRI fragment of approximately 814 base pairs; (e) inserting the second DNA sequence into the plasmid cloning vector at suitable site such that the first DNA sequence can act as a promoter for expression of the second DNA sequence upon transgenesis; (f) isolating a third DNA sequence including the 3' end of the porcine growth hormone gene, the DNA sequence including a SmaI/BamHI fragment of approximately 1000 base pairs; (g) modifying the 3' end of the third DNA sequence by treatment with Bal31 to delete regions identified as repeated sequences; (h) inserting the modified third DNA sequence into a SmaI site in the second DNA sequence to generate a plasmid expression vector; (i) introducing the plasmid expression vector or a linerized insert therefrom comprising the first, second and third DNA sequences into the male pronucleus of the fertilized pig ovum prior to fusion with the female nucleus to form a single cell embryo; and, (O) subsequently implanting the ovum into a female pig and allowing the embryo, resulting from introduction of the plasmid cloning vector into the ovum, to develop to maturity. Animals of the present invention can be produced in like manner as described therein, and the present invention can be utilized to increase the litter size or gamete production in animals as described therein.

5. Applications of the Invention.

The present invention is useful, among other things, for determining the presence of a transforming growth factor β in a sample. The method generally comprises the steps of: (a) providing a pituitary gonadotrope host cell that contains a nucleic acid construct a comprising an FSHβ locus control region as described above operatively associated with a promoter, which promoter is operatively associated with a nucleic acid encoding a detectable protein or peptide such as luciferase; (b) contacting a sample suspected of containing transforming growth factor β to said cell; and then (c) detecting the production of said detectable protein or peptide by said cell, the production of said detectable protein or peptide indicating the presence of a transforming growth factor β in said sample. The cells can be produced by in vitro transformation or derived from an in vitro culture, or obtained from transgenic animals that contain the cells. The contacting step may be carried out in an aqueous solution according to known techniques. Any transforming growth factor β that activates FSHβ expression in pituitary gonadotropes can be detected or determined/quantified by the method of the invention, including homodimers and heterodimers, and including bone morphogenetic proteins. The detecting step may be carried out by a step of (d) determining or quantifying the amount of said transforming growth factor β in said sample, which determining step may be carried out by known techniques such as by comparing the quantity of the detectable protein or peptide produced in response to the sample against that produced in response to one or more known standards.

An additional application of one embodiment of the invention is shematically shown in FIG. 1, in which an FSHβ switch (β-tetO DNA construct) is controlled by the ovine FSHβ promoter, which expresses the tet receptor only in pituitary gonadotropes. The tet receptor is not expressed anywhere else in the body of the host animal. When doxycycline (Dox) is present, it binds to the tet receptor and activates the tet operator, which in turn activates expression of the heterologous ovine FSHβ subunit. The excess FSHβ subunit joins with excess native FSHα subunit in gonadotropes (even where the FSHβ subunit and the FSHα subunit are of different species) to make active FSH. The "extra" FSH stimulates the ovary to ovulate more oocytes than normal.

Thus a further aspect of the present invention is a non-naturally occurring rollicle stimulating hormone, comprising and FSHα subunit from a first mammalian species (e.g., dog, cat, mouse, rat, cow, pig, horse, sheep, human) and an FSHβ subunit from a second different mammalian species (e.g., dog, cat, mouse, rat, cow, pig, horse, sheep, human), which may be obtained, isolated and purified from cells as described above in accordance with known techniques for the isolation of native FSH, optionally including an affinity purification step employing antibodies that specifically bind to a non-native FSHα or FSHβ subunit.

The present invention is explained in greater detail in the following non-limiting Examples, in which the FSHβ locus control region, tet receptor, tet operator and sheep structural FSHβ gene have been successfully associated and shown to increase FSH and ovulation in mice that carry the gene.

EXAMPLE 1

Identification of Sheep FSHβ Locus Control Region

The sheep FSHβ locus control region (FSHβLCR) was discovered to be located between −2.6 kb and −3.7 kb in relation to the transcription start site. It is absolutely required by the FSHβ promoter for expression of FSHβ in pituitary gonadotropes in vivo. Pituitary gonadotropes are the only cells known to express FSHβ and the LCR is necessary for this "targeted" expression.

EXAMPLE 2

Identification of Pig and Human FSHβ LCRs

The pig and human FSHβ LCR were identified based upon their homology to the Sheep FSHβ LCR by BLAST 2 homology analysis.

Figure 2:
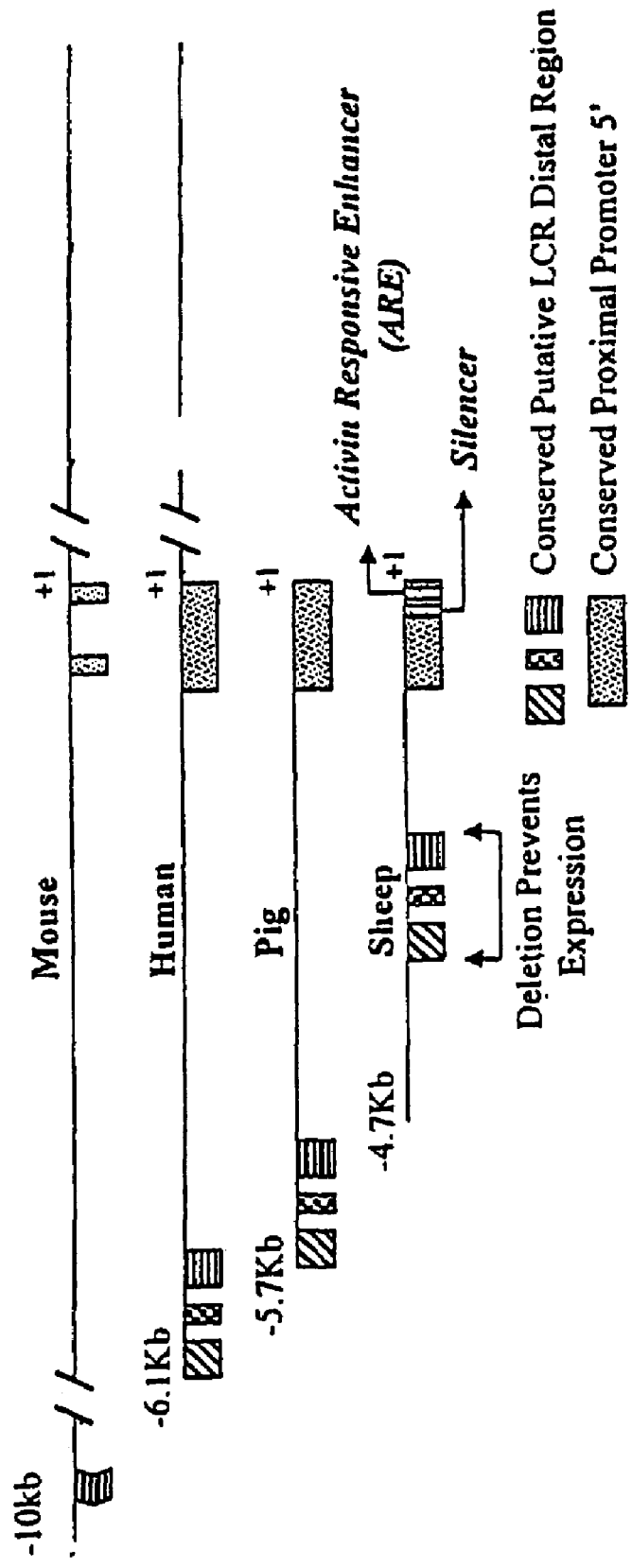
FIG. 2 schematically illustrates cross-species conservation of the FSHβ promoter and the FSHβ 5' locus control regions (LCRs).

Approximately 80 percent homology occurs in the proximal promoters of the sheep, pig and human FSHβ. The mouse has fewer areas of 80% sequence similarity. Areas of approximately 80 percent homology also occur upstream of all FSHβ promoters, as shown in the marked areas of FIG. 2. This high level of sequence conservation so far upstream, coupled with the fact that they are experimentally associated with gonadotrope-specific expression of oFSHβLuc, indicates that these sequences are locus control regions (LCRs).

The sequences for sheep, pig and human FSHβ LCRs are described herein as SEQ ID NO:1, SEQ ID NO:3 and SEQ ID NO:5, respectively. Also the sequences for the FSHβLCR/promoter units with intervening regions for sheep, pig and human are given herein as SEQ ID NO:2, SEQ ID NO:3 and SEQ ID NO:6, respectively.

EXAMPLE 3

Transgenic Mice

Figure 3:
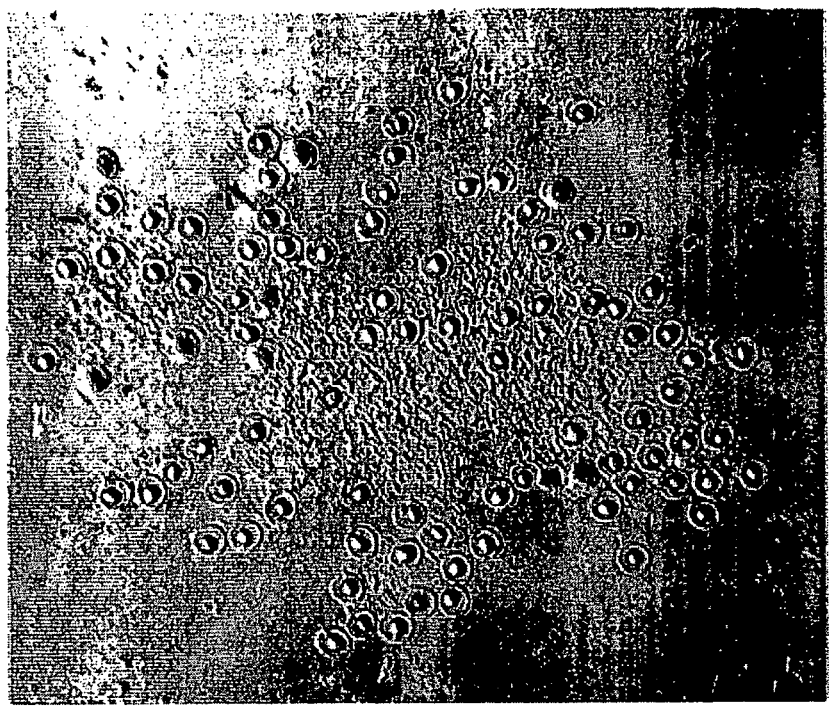
FIG. 3 demonstrates results obtained with transgenic animals of the present invention. Female mice (7 weeks old) were fed rat chow±Dox (6 gm/kg) and were put with males 6 days after feeding began. Females were checked for copulation plugs am and pm and were euthanized the morning plugs were found; uteri and ovaries were excised from each mouse and oocytes were freed from the ampulla and separated from cumulus cells with hyaluronidase (FIG. 3B). Oocytes were counted (see FIG. 3A). All Dox-fed mice ovulated within 5 days of male exposure except one (19 days) and it produced 90 oocytes. These 90 oocytes are shown in Figure B and appeared normal.
Figure 3:
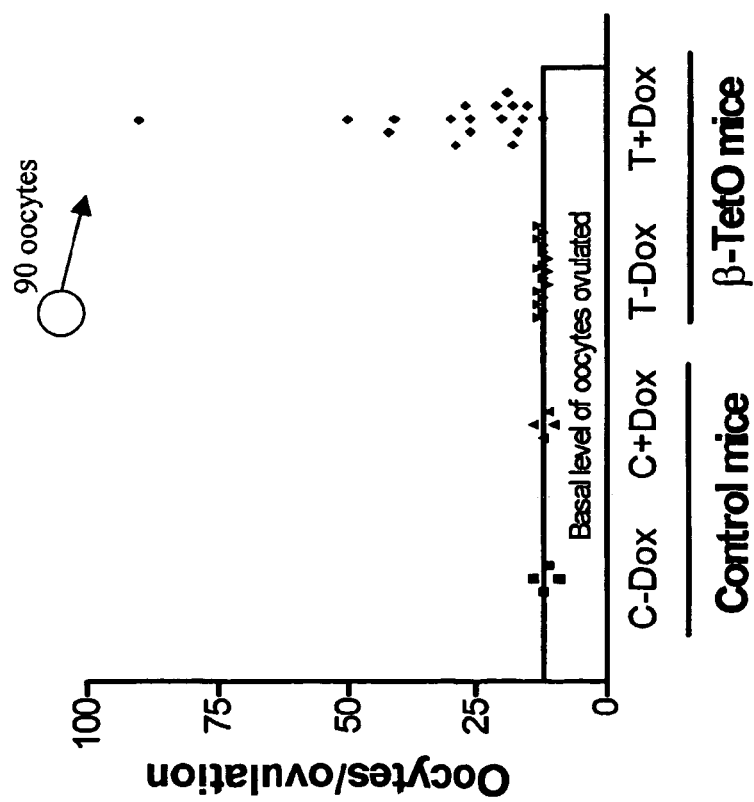

The sheep FSHβLCR was isolated along with its promoter in accordance with standard techniques and operatively associated with a new structural gene, the tet receptor, so that mice carrying this transgene expressed the tet receptor exclusively and strongly in pituitary gonadotropes. Linked to the FSHβLCR/tet operator gene unit was a second gene unit: the tet operator operatively associated with the structural gene for sheep FSHβ. As shown in FIG. 3, transgenic mice carrying this complex of two gene units (FSHβLCR/tet receptor plus tet operator/FSHβ gene) expressed the tet receptor exclusively in pituitary gonadotropes and produced FSHβ only in these same cells when tetracycline, or its doxycycline agonist, was administered. The increase in FSHβ production created more FSH which increased ovulation by 2.4-fold (from an average of 12±0.5 to 29±4). Ovulation of this magnitude is matched only by time-consuming treatments with costly fertility hormones.

The foregoing is illustrative of the present invention, and is not to be construed as limiting thereof. The invention is defined by the following claims, with equivalents of the claims to be included therein.

---

That which is claimed is:

1. A method of making a transgenic female mouse, comprising the steps of:
   (a) providing a recombinant nucleic acid comprising;
      i. a Tet operator response element and a minimal promoter;
      ii. a nucleic acid encoding ovine FSHβ operatively associated with said Tet operator response element and said minimal promoter;
      iii. an FSHβ promoter;
      iv. an FSHβ locus control region operatively associated with said FSHβpromoter; and
      v. a nucleic acid encoding a ligand-controllable receptor operatively associated with said FSHβ promoter, wherein said ligand-controllable receptor is a tetracycline-controllable transactivator fusion protein, and wherein tetracycline or an analog thereof acts as a ligand for said transactivator fusion protein; and
   wherein said receptor binds to said Tet operator response element in the presence of said ligand when expressed in a host cell; and (b) introducing said nucleic acid construct into a fertilized mouse oocyte;
(c) implanting said oocyte in a pseudopregnant female mouse;
(d) obtaining a chimeric offspring from said female mouse; and then
(e) mating said chimeric offspring to obtain a transgenic female mouse whose genome comprises and expresses said nucleic acid, wherein said transgenic female mouse exhibits increased FSHβ production and increased ovulation when administered said ligand than when not administered said ligand.

2. The method of claim 1, wherein said introducing step is carried out by microinjection.

3. The method of claim 1, wherein said nucleic acid comprises linear nucleic acid.

4. A method of enhancing the production of oocytes in a transgenic mouse, comprising the steps of:
(a) providing a transgenic mouse made by the method of claim 1, and
(b) administering said ligand to said mouse in an amount effective to (i) stimulate the production of FSHβ in said mouse above that found in a corresponding nontransgenic mouse; and (ii) stimulate ovulation in said mouse to a level greater than that found in the corresponding nontransgenic mouse.

5. The method of claim 4, further comprising the step of harvesting said oocytes from said animal.

6. The method of claim 4, wherein said administering step is followed by the step of:
(c) mating said mouse to produce an isolated litter of offspring therefrom, the size of said litter being greater than the size of an isolated litter produced by the corresponding nontransgenic mouse.

7. The method of claim 4, wherein said administering step is carried out by feeding said ligand to said mouse.

8. A transgenic female mouse whose genome comprises and expresses a recombinant nucleic acid, said recombinant nucleic acid comprising:
i. a Tet operator response element and a minimal promoter;
ii. a nucleic acid encoding ovine FSHβ operatively associated with said Tet operator response element and said minimal promoter;
iii. an FSHβ promoter;
iv. an FSHβ locus control region operatively associated with said FSHβ promoter; and
v. a nucleic acid encoding a ligand-controllable receptor operatively associated with said FSHβ promoter, wherein said ligand-controllable receptor is a tetracycline-controllable transactivator fusion protein, and wherein tetracycline or an analog thereof acts as a ligand for said transactivator fusion protein; and wherein said receptor binds to said Tet operator response element in the presence of said ligand when expressed in a host cell;
wherein said transgenic female mouse exhibits increased FSHβ production and increased ovulation when administered said ligand than when not administered said ligand.

* * * * *

SEQUENCE LISTING

```
<160> NUMBER OF SEQ ID NOS: 6

<210> SEQ ID NO 1
<211> LENGTH: 1765
<212> TYPE: DNA
<213> ORGANISM: Ovis aries
<220> FEATURE:
<221> NAME/KEY: misc_feature
<223> OTHER INFORMATION: Sheep FSHbeta LCR

<400> SEQUENCE: 1
catatattat atattactttt gtaatttaaa taaaggaaac aaattcaaat ggctaaaaca      60
aattcagatt taaaatttt taatataaat ttatttaatt ggaggctaat tactttacaa     120
tattatattg gttttaccat acatcaacat atatattaaa catttttta aattttacat     180 tataaatcat ttctcatgtg gccagaagaa aaggaggaaa agaatgctag accatagaag    240
gagcaagtcg agatatgagc acaaaggtac ttccctggtg gtctagtagt tatgaatctg    300
ccttgaaata caggggacgt gggttcaatt cctggtcagg gaactaagat cccacatgcc    360
acagggcaac taaccctgtg caccacaact acagagtctg catgccacaa ctaagaccca    420
aaataaataa accattttt aaaaaggaa attttttaaa aataggaaat taattttaaa    480 aattaattt aaaatttaat tttaaaattt aaaatttaat tttaatttaa aattaatttt    540
aaaaatagga aattaagtac cttcctcaca tcccatttt taaaaaagga tgtgaggaag    600
gtacttaatt tcctatttt aaaaacaacc ataaaggaat ggttgggaa aaaaaaaaa    660 cacctgtata agggaaaaaa ggatatagtc attgagtata tacagaggta gaaattctaa    720
ggatgctcac acagttgtgg acactggttc accagaattc acgagagaag tctgctgttc    780
gtttaaaata caatgtgatg agtgttaaca ttgagatgtg tactgggaac taaggaaaca    840
aaacaaagca ctggaaagag gatcgaatat tgaatatctt agatgaaaag aagagaaatg    900
tatctcaggc tcttatttt ctttcaagta agagagaaaa aaatacacat gattttggaa    960
```

```
aatggggagg tgtctcaagt caagaaagta agaatctgac ataaagctct cctcagtcaa    1020
cattttgtta aatattgagt caatattagg atactaaaat aatagggcta gaaataaaga    1080
tgggtgttat cactcagttt ccaaccagga aaactgaaac cactcctgat atgtaaaaca    1140
gagggaattt atccagggaa tgcattgtcc aagtgttaga attacagaga aaccagagag    1200
gagaaaggac aggactcaaa ggtcagcagt caccaaaagc cccactcatc ttcaggatta    1260
gaagaacaca ggtgggtttc cagagccaaa acatgagacc acttagcaga agctcaaacc    1320
acagagggtt tttctcacga aagctgggaa aactgagaaa agcttcctgt gtgacctgga    1380
ctcggagaaa atgcagctac taaccagaaa agaaaaatgt aaagggccca ggtttgatcc    1440
ctcatcaggg aactaagatc ccacaagcca tgcagagtgg ccaaagaaag aaaagggaga    1500
cagatgctct ttcttccttc tccttctatg ctccggtctc cctccccaga ggcttccgag    1560
agcagaacag agcaagaaca agaaatgcat cagctagcaa acaggttatg gaccagcaga    1620
gcgttaaggg aaactatgag tgatttgtgt ttcaatttgt tcaacaaaag tgaatctgtg    1680
cctactgtgg attagaaact cttcctattg ggaatacaaa ggtgaataag aaagacctct    1740
aaattttcat caataaaata tttcc                                         1765

<210> SEQ ID NO 2
<211> LENGTH: 4357
<212> TYPE: DNA
<213> ORGANISM: Ovis aries
<220> FEATURE:
<221> NAME/KEY: misc_feature
<223> OTHER INFORMATION: Sheep FSHbeta LCR + Promoter

<400> SEQUENCE: 2
catatattat atattacttt gtaatttaaa taaaggaaac aaattcaaat ggctaaaaca     60
aattcagatt taaaattttt taatataaat ttatttaatt ggaggctaat tactttacaa    120
tattatattg gttttaccat acatcaacat atatattaaa cattttttta aattttacat    180
tataaatcat ttctcatgtg gccagaagaa aaggaggaaa agaatgctag accatagaag    240
gagcaagtcg agatatgagc acaaaggtac ttccctggtg gtctagtagt tatgaatctg    300 ccttgaaaata caggggacgt gggttcaatt cctggtcagg gaactaagat cccacatgcc    360
acagggcaac taaccctgtg caccacaact acagagtctg catgccacaa ctaagaccca    420
aaataaataa accatttttt aaaaaggaa attttttaaa aataggaaat taattttaaa    480
aattaatttt aaaattaat tttaaaattt aaaatttaat tttaatttaa aattaatttt    540
aaaaatagga aattaagtac cttcctcaca tcccattttt taaaaaagga tgtgaggaag    600
gtacttaatt tcctattttt aaaaacaacc ataaggaat ggttgggaa aaaaaaaaa    660 cacctgtata agggaaaaaa ggatatagtc attgagtata tacagaggta gaaattctaa    720
ggatgctcac acagttgtgg acactggttc accagaattc acgagagaag tctgctgttc    780
gtttaaaata caatgtgatg agtgttaaca ttgagatgtg tactgggaac taaggaaaca    840
aaacaaagca ctggaaagag gatcgaatat tgaatatctt agatgaaaag aagagaaatg    900
tatctcaggc tcttattttt ctttcaagta agagagaaaa aaatacacat gattttggaa    960
aatggggagg tgtctcaagt caagaaagta agaatctgac ataaagctct cctcagtcaa   1020
cattttgtta aatattgagt caatattagg atactaaaat aatagggcta gaaataaaga   1080
tgggtgttat cactcagttt ccaaccagga aaactgaaac cactcctgat atgtaaaaca   1140
gagggaattt atccagggaa tgcattgtcc aagtgttaga attacagaga aaccagagag   1200
```

```
gagaaaggac aggactcaaa ggtcagcagt caccaaaagc cccactcatc ttcaggatta    1260
gaagaacaca ggtgggtttc cagagccaaa acatgagacc acttagcaga agctcaaacc    1320 acagaggggtt tttctcacga aagctgggaa aactgagaaa agcttcctgt gtgacctgga   1380
ctcggagaaa atgcagctac taaccagaaa agaaaaatgt aaagggccca ggtttgatcc    1440
ctcatcaggg aactaagatc ccacaagcca tgcagagtgg ccaaagaaag aaaagggaga    1500
cagatgctct ttcttccttc tccttctatg ctccggtctc cctccccaga ggcttccgag    1560
agcagaacag agcaagaaca agaaatgcat cagctagcaa acaggttatg gaccagcaga    1620
gcgttaaggg aaactatgag tgatttgtgt ttcaatttgt tcaacaaaag tgaatctgtg    1680
cctactgtgg attagaaact cttcctattg ggaatacaaa ggtgaataag aaagacctct    1740
aaattttcat caataaaata tttccaacaa cctttgtgaa aacaataaca cctaattagg    1800
aaatacacta gtcagataaa ccaggctcta agaggcttga cgttaggaga gaggtctgga    1860
agacctcttt tcatctcttg atcctcagca aattcatcca ccatccttat tctcaaatgc    1920
taaccttact tcctacttta ttgagaagat gaaattcatc acaggagagc ttgtacagac    1980
tgtcaccaca tctccctatc accatcatct gtctgcacca cacctcccta cccagcagca    2040
tctacactca caactctgcc tgatacagga tatgagctct tcatcctcca cagtccctcc    2100
agctgtgtct gaaatccatc tcttcctcca acaccattat ttttcactct ctactctatc    2160
atttgcacca ccatacaaac aagcagttat ttctcccatc ttaaaacata aaaatgaaaa    2220
gaaaattatc tttaccccac ttccaatgta tcacctgctt ttctcctcat ctttgaatca    2280
aaattcctgg aaaaaagctt tctatattta tctttctttg ggcttcccag tggcactaat    2340
ggtaaagaac ctgcctgtca atacaggaga tgtaaggaga tgtgtgttca gtccctgggt    2400
tgagaagatc cgctggagga gggcatggaa acccactcca gtattcttgc ctggagaatc    2460
ccatggacag aagagcctgg cgggctacag tccatggagt cacaaagagt tggacacgga    2520
ctgaagcaac agcacacgtg acattcatct cattttttatt catctcttgc caatcactaa    2580
aacacacacc agtcaggatt tgttcccct aactccaaag gaacttctca agccaagggt    2640
gtcagtgatc tttacaactg ccacgttatt atgcaatttc ccctaactta acctgtgagc    2700
actgtcgggt acagttgtca ctcactcctc ctgatacaca cactttactt gacttctggg    2760
ataccacatt ctcttcattc ctgtctttcc tcaacgaccc ttctgtttcc tttggataaa    2820
agaagaaaaa aagcttcatc ttatcctcga cctcttagtg ctggaataca ccaagctcta    2880 ccccttggtcc ttttgtcttc tctatttaca tacacccaat gccttggtaa tcttttcaag   2940
gcttatgtca atgactccca aattttttgcc tcagccaatg tatttctccc caaatccaga   3000
ttcagcattc tacatggatg tcttaaagat acctcaagtt caacatgtcc atactaaatt    3060
ccttatcttt tcaaaaaact tactgtatct ctagccatcc catttcagct ggtggcatat    3120
ttatctttca agtttctcag gccataatcc ttaaagttat ccttgactct tcctctcacg    3180
ctcaacattc atccatcaaa aaattctgtt tgctctactt tcacaatata tccagagtca    3240
agttatgtct tgttaattgc taccacacta gtctgaataa atatcgtttc ttacccaggt    3300
tgatgcaata gcatctaatg ggacttcctg tttctacctt tttaccccta cattagcaac    3360
acagcagtca aagggacccc ttcagaccta aatcagacga tgtcactcct ctactcaaaa   3420
ccctgcaatt ggtccctaat caacagtaaa aatcaaagtc tttatatcgg cctaaaccgt    3480
cctacatgac ttggcttctg ttacatctct gacatcatat cctaatattg tcaccattgt    3540
tcctttgcta gagccacact gcttaattag taaatatttg ttaaacaact caatcccagt    3600
```

```
ctccatggag ctcttagtct actgggagaa acaaagataa aggattaaaa agaagttgat    3660
aattaaagct ctcctcttct tcccagtcta aatgctgtca aatgaatgtt gaaggctgag    3720
gatttgcctg gggtggcagt gctataggag acatagcggg gaagcaagga catttcaggc    3780
aagatgaaca ctgcatatgc aaagagctag agagatgaat cagcagaaca tttaaagaat    3840
tacaagtaaa gcatcaaaga ataacatttg aaattagagg atctggatgt aaagaggaat    3900
acagtctata ttttagacag gagtcagatc atgaaagact ttctatttgt tttttctctg    3960
ctagttttca atctaccttc atagtaatta ttaaccatat cttttgata cacctcaaca     4020 gagccaaagc aatacttgaa agaattctg aattccccaa gttaaaggta caaagaaaa      4080 acccaaagtc aaatttaatt tgacaaggta aaggagtggg tgttctacta tatcaaattt    4140
aatctgtaca aaatcatctc tggtaacatt atttgtcctg atctactgcg tttagactac    4200
tttagtaagg cttgatctcc ctgtctatcc aaacactgat tcacttacag caagcttcag    4260
gctaacaccg ctcttactaa tacccaacaa atccacaagg tttagtttag tttcacacaa    4320
ttttgtataa aaggtgaact gagactagac tcagcta                              4357
```

<210> SEQ ID NO 3
<211> LENGTH: 1880
<212> TYPE: DNA
<213> ORGANISM: Sus scrofa
<220> FEATURE:
<221> NAME/KEY: misc_feature
<223> OTHER INFORMATION: Pig FSHbeta LCR

<400> SEQUENCE: 3

```
gaattcagga aagaggtctt ctgttcattt aaaatataac gtgatgtgtg ttaacactga      60
ggtagatact gggaattaag gaaacaatag aaagtactgg actgagaatg aatacggaat    120
actgtgtaaa gtggaacgag tgaatgtctc ctaggggaag ctacatctaa atggaatctt    180
gtagaagtgt ttgtaggaat agctcagatg aaaaggagat gaaaaggta cctcaggctt     240 aaggaatagc ctgattttca gaggtgggaa ggtgcttcaa gccaatgaag tgagattttt    300
tttttttttg gtcttttag ggttgcaccc acagcatatg gaagtttcca agctaaggtc      360
gaattggaac tgcaactgcc aacctacgcc acagtcacag caacatggga tctgagctgc    420
atctgtgaac tacactgcag ctcatggcaa caccagatcc ttaacccact gagcaaatct    480
agagatcaaa cctgtgccct aatggatact agccaggttc actaccactg agccacaacg    540
gtaactactg acgtgagaat ttaacatagg acctccttaa ataatgttca acattttgtt     600
taaatattga gttaattaat attattatac tagaacccag taataaaggg ctagaaataa    660
aaatgggtat tatcagtcac cttctaacca ggaaaacaga aactgctcct gataagagaa    720
gtcagaggat atttaatctg gggaatgcat tacctaagtt ttagaattgt tgagaagcca    780
gacaggaaat aaggaaaccc aaaaatcagt aaccatggga agctcccatc taccctcagg    840
attagagaga cacaaatgag gttcctggag ccaaaggtg agaccaccca gcagaagctc     900
aagccacatg tggagtttcc tcacaaaagc tgggaacact gagggaggag ctgtctgatg    960
caacctggac caagggagaa agtgcagcta ctgacaagga agaatgtaa aggagagaca    1020 tactccaacc ttcttcttct tttcactctc taatctcctt ccacagagac aaaaggctgc   1080
tgacacagca gcctaagaaa ggtagcctgc agaggtccct tctcccaaaa atcagagagc   1140
aaaacaggac aagaacaaaa aatgtatcag atagcaaaca ggctatggac aagcacaaca   1200
gaaagaaaat cagagtgatc tatgtttcac ttagttcaac aaaagtgtat cagtgctgga   1260
```

```
gttccccttg tggctcagca aaaacaaacc tgactagtat ccatgaggac tcacattcca    1320
tccctggcct cactcagtgg gttaaggatc cagcattgcc atgagctatg gtgtaggctg    1380
cagactcagc tcagatctgg tattgctgtg gctatggtgt aggccggacg gtacagctcc    1440
gattcgaccc cacctgagaa tttccatatg ccacaagtgc ggccctaaaa agacaaaaaa    1500
aaaaaaaaaa aaaaaaaaaa aaaagagtat tagtgcctac tgtggattag aaaccattcc    1560
tattgggaat acaaaggtga ataagaaagc tcactacatc ttcatcaata aatattttta    1620
ataacttttg tgagagcagt aacatctaac ttggaaatac acttatcaga taaactagac    1680
tataagaggc ttgacattgt gagaaaggtc tggggcctcg tgataggtca aggaaaataa    1740
ggttatttgg ggaaacctca gacctaaatg tggatggaag tataaatatg gacattagga    1800
atagcttccc aaattctgga tggcctctgt tttggcccct ctccaactaa tgcagttggt    1860
gagaattata aaccacagta                                                1880
```

<210> SEQ ID NO 4
<211> LENGTH: 5670
<212> TYPE: DNA
<213> ORGANISM: Sus scrofa
<220> FEATURE:
<221> NAME/KEY: misc_feature
<223> OTHER INFORMATION: Pig FSHbeta LCR + Promoter

<400> SEQUENCE: 4

```
gaattcagga aagaggtctt ctgttcattt aaaatataac gtgatgtgtg ttaacactga      60
ggtagatact gggaattaag gaaacaatag aaagtactgg actgagaatg aatacggaat     120
actgtgtaaa gtgaacgag tgaatgtctc ctaggggaag ctacatctaa atggaatctt     180
gtagaagtgt ttgtaggaat agctcagatg aaaaggagat gaaaaaggta cctcaggctt     240
aaggaatagc ctgattttca gaggtgggaa ggtgcttcaa gccaatgaag tgagattttt     300 ttttttttg gtcttttag ggttgcaccc acagcatatg gaagtttcca agctaaggtc       360
gaattggaac tgcaactgcc aacctacgcc acagtcacag caacatggga tctgagctgc     420
atctgtgaac tacactgcag ctcatggcaa caccagatcc ttaacccact gagcaaatct     480
agagatcaaa cctgtgccct aatggatact agccaggttc actaccctg agccacaacg      540 gtaactactg acgtgagaat ttaacatagg acctccttaa ataatgttca acattttgtt     600
taaatattga gttaattaat attattatac tagaacccag taataaaggg ctagaaataa     660
aaatgggtat tatcagtcac cttctaacca ggaaaacaga aactgctcct gataagagaa     720
gtcagaggat atttaatctg gggaatgcat tacctaagtt ttagaattgt tgagaagcca     780
gacaggaaat aaggaaaccc aaaaatcagt aaccatggga agctcccatc taccctcagg     840
attagagaga cacaaatgag gttcctggag ccaaaaggtg agaccaccca gcagaagctc     900
aagccacatg tggagtttcc tcacaaaagc tgggaacact gagggaggag ctgtctgatg     960
caacctggac caagggagaa agtgcagcta ctgacaagga agaatgtaa aggagagaca    1020 tactccaacc ttcttcttct tttcactctc taatctcctt ccacagagac aaaaggctgc    1080
tgacacagca gcctaagaaa ggtagcctgc agaggtccct tctcccaaaa atcagagagc    1140
aaaacaggac aagaacaaaa aatgtatcag atagcaaaca ggctatggac aagcacaaca    1200
gaaagaaaat cagagtgatc tatgtttcac ttagttcaac aaaagtgtat cagtgctgga    1260 gttcccctg tggctcagca aaaacaaacc tgactagtat ccatgaggac tcacattcca     1320
tccctggcct cactcagtgg gttaaggatc cagcattgcc atgagctatg gtgtaggctg    1380
```

-continued

```
cagactcagc tcagatctgg tattgctgtg gctatggtgt aggccggacg gtacagctcc    1440
gattcgaccc cacctgagaa tttccatatg ccacaagtgc ggccctaaaa agacaaaaaa    1500
aaaaaaaaaa aaaaaaaaaa aaaagagtat tagtgcctac tgtggattag aaaccattcc    1560
tattgggaat acaaaggtga ataagaaagc tcactacatc ttcatcaata aatatttta    1620
ataacttttg tgagagcagt aacatctaac ttggaaatac acttatcaga taaactagac    1680
tataagaggc ttgacattgt gagaaaggtc tggggcctcg tgataggtca aggaaaataa    1740
ggttatttgg ggaaacctca gacctaaatg tggatggaag tataaatatg gacattagga    1800
atagcttccc aaattctgga tggcctctgt tttggcccct ctccaactaa tgcagttggt    1860
gagaattata aaccacagta tggttcaatg agtagctctg ttttggagac agcagacct    1920
agatatgaac cttagccttg ctctttcagg ttccatagtt ttgggcaagt catttaaatg    1980
ttttcccatc tttcaaagag taataatagt aactccttta aaagttgtt taaaaattat    2040
atgtgatcat atatttgaag tgtttaagtg tctggggcat agtaggtgct caataaaaac    2100
ctgttaatat tttaaattga atgtgaaaag attgtatata cattactcat taaaacacat    2160
gaattcaata tagtcatata aatatacttt gtgaacacgc atagataaca taaaaagagt    2220
taatttgaaa tataaggtgg gaattcgtac catggcacag ggggttaatg atccacttgt    2280
ctctgtggca ttgctggctc aattcccagc ctggctcagt gggtaggatc tggcattgcc    2340
acagctatgg cataggccac agattcaact cggattcgat ccctagcctg gaaacttcca    2400
catgccacag gtgcagccat taaaaaaaaa aaaaaaaaat tctacattcc ttattactta    2460
cacaagtgct aaatcagccc ccagtacttt gataagtttt atctttgtca cacatgtttg    2520
ataaaatcat aaccctggat aaatccaagt atttgttacc catgagtctg aactcctgcc    2580
attaaattag gcaaaaaaaa aaaaaaaaaa aaaatcatgt ttagtggtct tgggttaaat    2640
ttttttacca taaacctcaa atggtccctt aatactggta ggcaatttta ctacctatac    2700
ctaactcacc aatgactcag tccctctacc agtctcatac aaatattaag ccttggatct    2760
ctcaatcctc aacaatgcat ccactacctt tactctcaga tgatgatctt acttcctact    2820
ttactgagaa aatgaaaaca atgacaggag agtctgtata aagcccatca cccaccaaac    2880
actcaccatc ttctgcactc accacaccct cccaaccagc agcatctcta cccatgactc    2940
tgcctcctgc ccacaacagg atgagctctc ctgtttaaag ccagtcattc tacttgtgct    3000
ctaagatcca tctcttctca tagtctacct aagaacactg aagaaatttt cctctcttgc    3060
tccaacatca tttttctctc aatcatttgc atcaccaaac taacagttat gtcttcagtc    3120
ttaaaacata aaaatcaaaa ggaaattatc tttaccccac ttccatgtga ccaaatcacc    3180
tgtttttttc ctcatctttg tatcaaaatt ctggggagaa aaagttcaac acttttttg    3240
taatggtcac acctgtggca tataggagct ccttttgccac agccacagta atgccggacc    3300
caagttgcat ctgcaactga cacgcagttt atggcaatgc ggatccttag tccactgaga    3360
gaggccaggg attgaattta tatcctcagg aaaacaatgc tgggttctta acttgctgag    3420
ccaaatgtga actcctcaat tcttttttat tcatttcttt ccaatcactc agtctgctct    3480
tttattgaat tatagctgat ctataatggt atgttagttt ctggtgtata gcaaagtgat    3540
tcagttatac atacatatta cttttcacat tcttttccat gacagtttat cacaggatat    3600
tgaatatagt tgcgatacag taggaccatt ttgtttatct atcctatata taatagtggt    3660
taatcccaaa gtcccaatcc aaaccatccc caccctcctg cccttggcaa ctacaagtct    3720
```

```
gttctccatg tctgtgagtc tgtttctgtt ccattcattt gtgtcataat ttagattcca    3780
catataattg taatcatatg gtatttgtct ttctctttct gacttgcctc acttagtatg    3840
acaatccatg tagccacaaa tgtcttgaca attacttaaa cacacaccaa tcagggtttt    3900
gtttctctca ctccaaagga gcttctctag ccaaggacac tggcaacatt tatgctgcca    3960
cacgcattgc taacctgtca gcagcatttg gtacagttgt cacttgctcc tcctgacaaa    4020
ctggctttac ttgatttctg ggacaccaca ttctctccat tcctttcttt cctcaatgac    4080
ccttctgttt cctttgggca aaggaaggga aaaaaacttc atcttattct tgacctctta    4140
atattagcac acaccagcct ccactcttgg tcctttatc ttctctattt atacttactc    4200
ccttggtaac ttcttcaagg ctcatgccaa ttatacattt tagctagcat atttctccca    4260
aaatccagat tcaccattct acttagatat cttaagctca acctatccat accgaactcc    4320
ttatcatttt cccaaactta ctatatttat agccatccca tttcagttga taacaaattc    4380
atccttcaag tcactcaggc cagaatcttt agagtcatct tcactctttt cttttctca    4440 cactcaggat tcatccatca gaaaatcctg ctggctccac tttcaaaata catatgaaat    4500
cagattactt tgattatttt attactacta ttactgaaca gatagcactt ctcacccaag    4560
ttgctgcaag agcatctaat aggacttcct gtttctacct cccccacccc catattagca    4620
accaggcagc cagagggtcc tttaagactt aaacctgatt tatcactcc tatactcaaa    4680 accctgcaac tggtccccaa acaccgacag taaaaactga agtctttaca ttgaactaaa    4740
aagtccgaca ttatttgact tctgccacat ctgtgacatc atatcctcat atttccatca    4800
ttgttccttt tctccagcca aggagcttaa ttaattaata agcttaatta attgctcaat    4860 taataaaatat ttgttaaatc aatctcagtt tccatggagc tcatagtcta ctgggagaga    4920
aaaatatata aagaataca aaaagaaggt aattaaagct ttcctcaatc tcccattcct    4980
aaacaatgac aagtgaatgt tgaaggttga gaaatttgcc aggggtggg agtagtatag    5040 gggacattgg gaggaagcaa ggacatttca ggaaggatga acatggcaca tacaaagacc    5100
tagagaaatg aatcagcaga acatttaaag aattacgagt aaagcatcaa agaataaatt    5160
ttaagattaa ggaatctgaa tatgggaagt aaacataaat ataatttaca ctttataaaa    5220
gagtataatc atgaaagact ctctatttgt ttcttcctt acagctgtca gtctagtctc    5280
agagtaactt attaaccata tatatatata ttttttgaca cacctcaaca gtgccaaagc    5340
aatacttgga aaggattcta aattccccaa attaaatata caaagaaaaa acccagagtc    5400
agacttaatt tgaaaaggta aaggagtggg tgttctacta tatcaaattt aatttgtaca    5460
aaatcatctc tggtaacatt attttttcctg ttccactgtg tttagactac tttagtaagg    5520
cttgatctcc ctgtctatct aaacactgat tcacttacag ccagcttcag gctaacattg    5580
atcttactaa tacccaacaa atccacaaag tgttagtttc acatgatttt gtataaaagg    5640
tgaactgaga ctagattcag cccacagctt                                      5670
```

<210> SEQ ID NO 5
<211> LENGTH: 1947
<212> TYPE: DNA
<213> ORGANISM: Homo sapiens
<220> FEATURE:
<221> NAME/KEY: misc_feature
<223> OTHER INFORMATION: Human FSHbeta LCR

<400> SEQUENCE: 5

```
tatatgttat ttattacttt ataatttaaa taaagtagat atttctaaat aatatttaa        60
```

```
atgacaaaaa agaataaaat aattagaaaa taaaatatat taaacattta aaaccttaca      120
ttgtaaaaca tatatcacat gggcaaagga aaggaggaaa ggatccgaga acatagaagg      180
agcaggtaat ttatcaaggc atgaacacgg gtgcttaatt tcctattttg aggccaggca      240
tggtggctca cacctgtaat cccaacactt taggaagcca aggtgggtgg attgcttgag      300
tctaggattt tgagaccagc ctggccaaca tggcgaaatc ctgtctctac taaaaatact      360
aaaattaacc agtcatggtg gtggtgtgcc tttagtccca gctactctgg tggctgaggc      420
acaagaatca cttgaacctg ggaggcagag gttgcagtga gctgagactg tgccacttca      480
ctccagcctg ggtgacagag taagattctg tctcaaaaaa tatgtatata tacacacata      540
taatagatac ataaacatat ataaatatat aatatataaa tatatatatt atatataata      600
tataaacata tataaaatat atatatatat atatataaa accaaacata aaggaataat       660
tttgggggaa aatcttcata aatgaaagaa caacataggc tgttgagtat atgcacagaa      720
attcaagaga tcttccagca attgaagaca ttggtttacc agaattcaca aaagaagtca      780
gctgtgcatt taaagtagaa tgtgatgagt gttaccactg aggtaggaac tgggaactaa      840
ggaagcgtaa gacagaaagt gctgaactga gagttgggca ttggaggctg tgtaaggcag      900
ggtaagtgaa tgtctcctag aagctacctt taaatggagt tttgaagtac ttgtaggagt      960
agcttaggtg aaaagaagag gagaaacatg tatcaggcag agggactaga accttattac      1020
cttcaaagaa gaagcaaaaa gaatacatgt gactttgagg tggtgggagg tgctttaagc      1080
caatataggt gaatttgaca taggacttcc ctaaataatg ttcggtcatt tgttaaatat      1140
tgagtgatat atcactgtat taaagcccaa gagttgcttt tatatagaaa gaagaaaaaa      1200
gcccaagaga gttttatttc tagagggaat attttctaga aataaaggaa ggtgtatcag      1260
ccagtttcta gtcaggaaaa cagaaatcac acctgatatg caaaatagag gaaaatcagg      1320
gaattcatta atccagagat ttggttgctc aagtattaga ttgctgaaaa gccagacagg      1380
gaatatgagg caatcagaga taagtattag tgacaagctc catttatgtg caggattgga      1440
gggacatagg tggggttccc agaagccaga aggtgagacc acctagcaga agctcaaacc      1500
acagctgggg tttcctcaca aaagctggga ccaccaggag gagctgtcca atgggatctg      1560
gagccaggga gatcatgcag tcactaccag gaagggaagc agaatgtaaa aggtagagag      1620
aaatactcca actgcttcct tgcattcact ttccaatctc cattcacaaa ggcaaaaacc      1680
tgctaataca gcagagtggg aaaagcagcc tgccaaggtc ctttctccca caaaacagag      1740
cacaaaacca agcaaaaaca aggaatgcat ttgatagcaa acaggctatg gaccaaccca      1800
acataaaaga aatgatgagt gatttctttt ttcatttggt tcaagaaaag tatttcagta      1860
actattatgt aacagaaatt ctatttattt tgggaattc aaaggtgaat aaaaaagaac       1920
tctaaatttt tatcaataaa atatttc                                         1947
```

<210> SEQ ID NO 6
<211> LENGTH: 6730
<212> TYPE: DNA
<213> ORGANISM: Homo sapiens
<220> FEATURE:
<221> NAME/KEY: misc_feature
<223> OTHER INFORMATION: Human FSHbeta LCR + Promoter

<400> SEQUENCE: 6

```
tatatgttat ttattacttt ataatttaaa taaagtagag atttctaaat aatatttaa       60 atgacaaaaa agaataaaat aattagaaaa taaaatatat taaacattta aaaccttaca     120
```

```
ttgtaaaaca tatatcacat gggcaaagga aaggaggaaa ggatccgaga acatagaagg      180
agcaggtaat ttatcaaggc atgaacacgg gtgcttaatt tcctattttg aggccaggca      240
tggtggctca cacctgtaat cccaacactt taggaagcca aggtgggtgg attgcttgag      300
tctaggattt tgagaccagc ctggccaaca tggcgaaatc ctgtctctac taaaaatact      360
aaaattaacc agtcatggtg gtggtgtgcc tttagtccca gctactctgg tggctgaggc      420
acaagaatca cttgaacctg ggaggcagag gttgcagtga gctgagactg tgccacttca      480
ctccagcctg ggtgacagag taagattctg tctcaaaaaa tatgtatata tacacacata      540
taatagatac ataaacatat ataaatatat aatatataaa tatatatatt atatataata      600
tataaacata tataaaatat atatatatat atatatataa accaaacata aggaataat       660 tttgggggaa aatcttcata aatgaaagaa caacataggc tgttgagtat atgcacagaa      720
attcaagaga tcttccagca attgaagaca ttggtttacc agaattcaca aaagaagtca      780
gctgtgcatt taaagtagaa tgtgatgagt gttaccactg aggtaggaac tgggaactaa      840
ggaagcgtaa gacagaaagt gctgaactga gagttgggca ttggaggctg tgtaaggcag      900
ggtaagtgaa tgtctcctag aagctacctt taaatggagt tttgaagtac ttgtaggagt      960
agcttaggtg aaaagaagag gagaaacatg tatcaggcag agggactaga accttattac     1020
cttcaaagaa gaagcaaaaa gaatacatgt gactttgagg tggtgggagg tgctttaagc     1080
caatataggt gaatttgaca taggacttcc ctaaataatg ttcggtcatt tgttaaatat     1140
tgagtgatat atcactgtat taaagcccaa gagttgcttt tatatagaaa gaagaaaaaa     1200
gcccaagaga gttttatttc tagagggaat attttctaga aataaaggaa ggtgtatcag     1260
ccagtttcta gtcaggaaaa cagaaatcac acctgatatg caaaatagag gaaaatcagg     1320
gaattcatta atccagagat ttggttgctc aagtattaga ttgctgaaaa gccagacagg     1380
gaatatgagg caatcagaga taagtattag tgacaagctc catttatgtg caggattgga     1440
gggacatagg tggggttccc agaagccaga aggtgagacc acctagcaga agctcaaacc     1500
acagctgggg tttcctcaca aaagctggga ccaccaggag gagctgtcca atgggatctg     1560
gagccaggga gatcatgcag tcactaccag gaagggaagc agaatgtaaa aggtagagag     1620
aaatactcca actgcttcct tgcattcact ttccaatctc cattcacaaa ggcaaaaacc     1680
tgctaataca gcagagtggg aaaagcagcc tgccaaggtc ctttctccca caaaacagag     1740
cacaaaacca agcaaaaaca aggaatgcat ttgatagcaa acaggctatg gaccaaccca     1800
acataaaaga aatgatgagt gatttctttt ttcatttggt tcaagaaaag tatttcagta     1860
actattatgt aacagaaatt ctatttattt tggggaattc aaaggtgaat aaaaaagaac     1920
tctaaatttt tatcaataaa atatttcaaa aacctcaatg agagtaatgg cattaactag     1980
caaatatgct aatgagatga gctagccata agaggcttag aattgagaga aaggtctggg     2040
ggcctcttga caggccaaat tcagagctgt ttgtgggaat ctctgaccta actgcaggtg     2100
gaaatataaa tatgggcatt tagaatagtg gcccaaactt tggatgattt ctgtcttggg     2160
gtctctccaa ttaatgggat tgatgagaac tgtagaccac tgaggtcacc atggctcaat     2220
gaatagtccc ctggctttgg agtcaaactg acctgaatat gaaccccagc tttgctactt     2280
acaggttgca tttatcctca gttttctcat cttttcaaaga agaacagtaa cttcttaaa     2340 aggttattgt aggctgggtg cagtggctca cgcctgtaat cgcagcactt tgggaggcgg     2400
aggctagtgg atcacttgag gccaggagtt ggaaactagc ctggccaaca tggtgaaact     2460
ctgtctctac aaaaagaaat ttaaaaaatt ttgctgggtg tggtggcaca cacctggaat     2520
```

```
tccagctacc tgggaggccg aggcatgagc atcacttgag tctggaaagc agagggttgc    2580
agtgagccaa gattgtacca ctgtactcaa gcctgggtga cacagtgaga ccttgtctaa    2640
aaaaaaaaag gttattgtgt tattgtaaat attgtatatg aacttctatt taacatgttt    2700
agttaaatgc ctgtgtaatt gtccaatgtg ctcttctagc tcactgcaca gacaaaactg    2760
attcactgaa atcatggaat tgcagcaaag aacaaatcta attaatgtag gtcaaacggg    2820
aggactggag ttattattca aatcagtctc cctgaaaact cagaggctag ggttttatgg    2880
ataatttggt gggcagggga ctagggaatg ggtgctgctg attggttggg gaatgaaata    2940
gtaagattgt ggaaaactgt cctccttcat tgagtctgct tccgggtgta ggccacacga    3000
ccagttgagt catgaagcat gcgtccaagt ggagtcagtt tgttgccaga atgcaaaagc    3060
ctgaaaaatg tctcaaatga tcaactgtag gctccacaat aatgatatta tctataggag    3120
caattgggga agtaacaaat cttgtgacct ctggacacat aactcctgaa ctagtaaggg    3180
attataaaaa ccatgcctat atcttatcag aattcaggtc cccccataat cctaatctca    3240
cagcatttca tttgtttaga aaggccattt tcagtccctg agcaaggagg gggttagttt    3300
taggatagga ctattatcct tgcttcgtta aactataaac taaattcctc ccatggttag    3360
cttggcctac acctaagaat gagtgagaac agccagcctg tgaggctaga ggcaagatgg    3420
agtcagccat gctagattta tctcactgtc ataacctttg caaaggcagt ttcacctggg    3480
acataggagg tactcaatga aaagaagct attaatatta atattttaaa aatgaattta    3540
aggaactaat actatgtaca tattagtcat taaaacaaag tggttcattt acattcacac    3600
aaataaatct tgtgattata cataggtaat atgaaaaact ttgttttctt tcataataca    3660
aggtattagc aatagatata gtaatgttag cattcctttg gaaaaatga aaagattat     3720 aattttccaa gaatcattag tatttttatt taatatacat aatataaaat ttattcattc    3780
tataacttgg aaatatgctt gcttaccaat tactgacaga tttcaaaata tttctatact    3840
cacaatattc atttacataa atattgattt ggtacttaca atgtgtactg ctatgctaag    3900
ttttgtcttt gtcaaacata ttttataaaa tcataatcct agatgaatcc aacttttggt    3960
aacccacgtg cctgaacccc tgctgttaac aggcaaagtg tggtaggtac agatctatac    4020
ctaccacctt cctctaccca ccagcatctg cacccaccac ccctccccac ccaccattat    4080
ctataccaac caccctccc aacctaccag catctgcacc caccacaccg cccacccacc     4140
accatgtaca ctcaccacac cttccagcca tcaccatctg cacccatcac tcctccccat    4200
ccacaagcat ctgcacccac cacatttccc tacctaccag catcttcact caccacctct    4260
ccacccacca gcatctgcac ccacaacccc tcctcaccca ccagagtctg catccatcac    4320
acttgcccac tcgctagcat ctgcaccatc aagctctgcc ttcttgccta atacgggatg    4380
agctctccat ggttctgcct aaagacaatg cttccactcc tcttctataa cccatttcct    4440
tttacctctt caagtacact tcagaacttc tctctccttc tgataccaac ttttttccact   4500 ttactcaatc attcctatca ccatacaaac gtgtttattt ctcccatctt aaagttaaaa    4560
atcaaaagaa aattgtctgc ggccaggcac ggtggctcac gcctgtaatc ccaacacttt    4620
gggaggccaa ggagggttgg atgacttaag gttaggagtt caagaccagc ctggccaaca    4680
tggtgaaacc catctctact aaaaatacaa aaattagcca ggcatggtgg cacatgcctg    4740
tagtctcagg tacttgggag gctgaggcca gagaatggct tgaacccggg aggcagaggt    4800
tgcagtgagc cgagattgtg cccttgcact ccagcctggg tgacagagtg agactccatc    4860
```

-continued

```
tcaaaaataa aaaataaaaa taaaacaaaa gaaagttatt tttacccaac atccacatta    4920
accaaatacc catttcttta ttgatctttg taaaaaaaag ctcttggaaa aattgtctat    4980
attcactatg acttatctcc tccaaatcac ttaaacacat accaatcagg tttttgtttt    5040
catcattcca aagtaacttt tacagccaag gacagtagcg aactttacat cgcatatgca    5100
ttgtgaagtt cttgatcctc atcttactta acctgtcagc agtatctgac acaggtgtca    5160
ctggctcctc cctgagatgc tctcttatt tggcttttgg gacaccatat tctcccatt     5220
cctactttcc tcaatggccc tcctcagtct cctttggaaa gaggaaaaag aaacttcatt   5280
atctcctgga tgtagtacaa acaactcaag ctcaacatgt gcatactgaa ctccatttcc   5340
ttttcccaaa cttcgacatt tacagccatc cccttcagc tgatagcaag tttatccttc    5400
cagctactca aaccagaatc tttagagcca tccttgaccc ttttcctcct ctcacactca   5460
acatctatcc atcagaaaat tttgttggtt ctactttcaa aatgcataca gagtcagagc   5520
atgtctcatt acctccaata gctaccatac tagtctgaac aaacatcatt tctcacctgg   5580
gttattgaac aaacatcatt tctcacctgg gttattgata gcatcctaac gggtcttcct   5640
gtttcttggt tcccctatat tagcaacaca gcagtcagag gagtcctttt agaactcaat   5700
cagatcatgt cacgtcactc ctctacttaa aatccttcaa tgggtcccat tacacaaaga   5760
gtacaaacca gagcccttac actggtctac aagttccaac atttgactcc tgttatctct   5820
ctgacatcat attctaatat tactgctgtt gtccttttgc tccagtcaca ctgtttgatt   5880
agtaaatatt tattaaacaa agcaatccta gtctccaaag agatcatagt ttattggagg   5940
aaacaagagc ctataaatgg ttacacacag aaggtagtga ttatggttct ccctcacctc   6000
ccatcctaaa ctttgacagg tgaaactccc ctggatgttg aaggttgagg aatttgccag   6060
ggttcagggt ggtgttggag gaggcaggga ggaagcaagg acatttcagg caggaagaac   6120
attacatgca aagatctaaa gatatgaatc agcaacatat ttatggaatt acaagtaaag   6180
tagaaagttc ttgctaaaac atcaaaaaat aaagatttgt gattaggggg ccagaatgtg   6240
ggagggaaag agagatacag ttcacacttt agacaggagc cagatcatga aatgttttct   6300
ctttgtttgt ttcttccttc acagcttttg atatgctctt ggagcaattt attaaccata   6360
tttttaatg catctcctga acagagtcaa agcaatactt ggaaaggact ctgaatttcc    6420
tgatttaaag atacaaaaga aaaatctgga gtcacaatta atttgagaag gtaaaggagt   6480
gggtgtgcta ctgtatcaaa tttaatttgt acaaaatcat catctctagt aacattattt   6540
tttctaatct actgcgttta gactacttta gtaaagcttg atctccctgt ctatctaaac   6600
actgattcac ttacagcaag cttcaggcta gcattggtca tattaatacc caacaaatcc   6660
acaaggtgtt agttgcacat gattttgtat aaaaggtgaa ctgagatttc attcagtcta   6720
cagctcttgc                                                          6730
```